US012144972B2

(12) United States Patent
Heisiep et al.

(10) Patent No.: US 12,144,972 B2
(45) Date of Patent: Nov. 19, 2024

(54) SYSTEM FOR MONITORING THE DISPENSING OF AN ADMINISTRABLE SUBSTANCE, PROTECTING ELEMENT AND DISPENSING DEVICE

(71) Applicant: Boehringer Ingelheim International GmbH, Ingelheim am Rhein (DE)

(72) Inventors: Joerg Heisiep, Ingelheim am Rhein (DE); Andree Jung, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 953 days.

(21) Appl. No.: 17/268,101

(22) PCT Filed: Aug. 16, 2019

(86) PCT No.: PCT/EP2019/071993
§ 371 (c)(1),
(2) Date: Feb. 12, 2021

(87) PCT Pub. No.: WO2020/035585
PCT Pub. Date: Feb. 20, 2020

(65) Prior Publication Data
US 2021/0275753 A1  Sep. 9, 2021

(30) Foreign Application Priority Data
Aug. 16, 2018 (EP) .................................. 18189322

(51) Int. Cl.
*A61M 5/315* (2006.01)
*A61M 5/32* (2006.01)
(Continued)

(52) U.S. Cl.
CPC ...... *A61M 5/31566* (2013.01); *A61M 5/3202* (2013.01); *G09B 9/00* (2013.01);
(Continued)

(58) Field of Classification Search
None
See application file for complete search history.

(56) References Cited

U.S. PATENT DOCUMENTS 7,002,476 B2    2/2006  Rapchak
7,093,736 B2    8/2006  Maietta et al.
(Continued)

*Primary Examiner* — Thomas S McCormack
(74) *Attorney, Agent, or Firm* — Calderon Safran & Wright P.C.; David S. Safran

(57) ABSTRACT

A system, a detection device, a method, a use, and a computer program product for monitoring an actual or simulated preparation, performing, and/or post-processing of a dispensing—referred to as dispensing process below—of an administrable, preferably pharmaceutical, substance, with a dispensing device for dispensing the substance, whereby the dispensing device has at least one sound generator, which is designed in the dispensing process to generate at least one sound event, specific to a property or change in state of the dispensing device, in an acoustic signal, and with a detection device for checking the acoustic signal for the at least one sound event, in order to make possible a detection of the property or change in state of the dispensing device.

32 Claims, 14 Drawing Sheets

(51) Int. Cl.
*G09B 9/00* (2006.01)
*G09B 23/28* (2006.01)
*G16H 20/13* (2018.01)
*G16H 20/17* (2018.01)
*G16H 40/67* (2018.01)

(52) U.S. Cl.
CPC ............ *G16H 20/13* (2018.01); *G16H 20/17* (2018.01); *G16H 40/67* (2018.01); *A61M 2205/3375* (2013.01); *G09B 23/285* (2013.01)

(56) References Cited

U.S. PATENT DOCUMENTS

| | | |
|---|---|---|
| 2005/0199527 A1 | 9/2005 | Ellis et al. |
| 2009/0131875 A1 | 5/2009 | Green |
| 2011/0114595 A1 | 5/2011 | Heiberger |
| 2013/0099929 A1 | 4/2013 | Ophardt et al. |
| 2014/0207080 A1 | 7/2014 | Allerdings |
| 2014/0251851 A1 * | 9/2014 | Huntley ............... B65D 51/248 206/459.1 |
| 2014/0297312 A1 | 10/2014 | Bangera et al. |
| 2015/0290396 A1 | 10/2015 | Nagar et al. |
| 2016/0166766 A1 * | 6/2016 | Schuster ................ G01F 22/00 702/54 |
| 2017/0154548 A1 | 6/2017 | Krauss et al. |
| 2018/0099084 A1 | 4/2018 | Schabbach et al. |
| 2019/0015596 A1 | 1/2019 | Saint et al. |

* cited by examiner

SYSTEM FOR MONITORING THE DISPENSING OF AN ADMINISTRABLE SUBSTANCE, PROTECTING ELEMENT AND DISPENSING DEVICE

BACKGROUND OF THE INVENTION

Field of the Invention

This invention relates to the monitoring of an actual or simulated preparation, performing, and/or post-processing of a dispensing of an administrable, preferably pharmaceutical, substance.

This invention relates in particular to the monitoring of the dispensing of an administrable substance in connection with operational monitoring of a dispensing device or in connection with the determination of so-called patient compliance, also called compliance or adherence.

In the case of operational monitoring, the process of an actual or simulated dispensing of an administrable or pharmaceutical substance is monitored with respect to indicators, which do or do not indicate a proper or complete operation, in particular administration.

To determine patient compliance, the extent to which and/or the intervals at which a medication is taken is/are monitored. The result of the monitoring, in particular, i.e., information on an actual administration or medication, can subsequently be checked to ascertain whether the latter corresponds to a preset value, which can be present in the form of, for example, a physician's prescription, or whether it deviates therefrom.

Based on the results of the operational monitoring or the determined patient compliance, measures can automatically be introduced. Such measures are introduced in particular when it is determined that there is a malfunction—it can be by technical defect or operating error—or that the administration of medicines deviates from this preset value.

Both results of operational monitoring and the determined patient compliance can be used as measures to inform or to alert a user (patient) or third party, such as a medical practitioner or a medical system.

Description of the Related Art

U.S. Pat. No. 7,002,476 B2 relates to a medicine-dispensing device that is coupled to a transceiver for wireless control, which transceiver accesses a set of control data from a server. A set of instructions is downloaded in order to instruct a user via the transceiver on how to use the dispensed medication.

In order to safeguard the medication, an audible or visible indication can be given after time elapses.

U.S. Pat. No. 7,093,736 B2 relates to an arrangement with a blister, which can be moved between two positions. An alert is given when a cycle period has ended. An alert unit is set back when the blister is accessed for the purpose of removing the medicine. To this end, a special device with a mechanism and a sensor system is proposed, which is designed to monitor access to the blister.

SUMMARY OF THE INVENTION

The object of this invention is to simplify or to improve the monitoring of the actual or simulated dispensing of an administrable substance.

This object is achieved by a system, a detection device, a method, a protecting element and a dispensing device as described herein.

A first aspect of this invention relates to a system for preferably acoustic monitoring of an actual or simulated preparation, performing, and/or post-processing of a dispensing of an administrable, preferably pharmaceutical, substance. This actual or simulated preparation, performing, and/or post-processing of a dispensing are combined below under the term "dispensing process".

The system according to the proposed solution has, on the one hand, a dispensing device for dispensing the substance, and, on the other hand, a detection device for checking an acoustic signal.

In terms of this invention, the term "dispensing device" is defined as a device that is designed for dispensing the substance for the purpose of administration. The dispensing device is preferably a device for dispensing one or more doses or portions of the substance, which (in each case) are suitable for complete and/or direct administration to a patient because of their amount, their volume, and/or their form.

Thus, the term "dispensing device" comprises, on the one hand, packages such as blisters or containers such as reservoirs, from which the pharmaceutical or other administrable substance can be removed for the purpose of administration. In this case, the substance can be removed in particular manually in discrete individual doses, for example as capsules or tablets, or in the form of powders or granulates. Additional examples of dispensing devices are injection systems, such as autoinjectors and syringes, sprays, inhalers, or dispensers for liquids, creams or gels.

In terms of this invention, the term "actual dispensing" is defined as that the latter leads or is to lead to the administration of the substance. In this case, this can be the injection of an injection solution, the nebulizing of an inhalable substance, or the removal from a package of a substance that can be handled manually.

In terms of this invention, the term "simulated dispensing" is defined as in this case the operation of a dispensing device for administrable substances for testing or training, without this operation leading to or being able to lead to an administration of the substance, or wherein the substance is a placebo. The operation is carried out, however, in the same way or similarly to the operation of a dispensing device for actual dispensing or administration. What is meant in this case is in particular the preparation and operation of a dispensing device that contains a placebo, for example a placebo inhaler for inhalation training or a placebo autoinjector for injection training.

When hereinafter only "dispensing" is meant, this comprises the actual dispensing, the simulated dispensing, or a combination of simulated and actual dispensing unless something else is explicitly described or is obvious from the context.

"Administrable" is preferably a substance when it is suitable and intended for direct application to a patient (human or animal) or for direct ingestion by a patient and/or is present in a dosage form and amount that is usual for personal, medical, or clinical use.

The dispensing device according to the proposed solution has at least one sound generator. In terms of this invention, a structure that is designed to generate or to trigger a sound event in the acoustic signal is referred to as a "sound generator."

In this case, the sound generator can be set up especially for the purpose of sound generation or can be formed by a structure that is used for another primary purpose, but which generates or triggers a sound event when used. The sound generator can be arranged in one or more pieces and in one or more positions of the dispensing device and/or packaging of the latter.

A sound generator preferably consists of at least two parts or sections that correspond to one another and that produce or trigger the sound event in the case of relative movement to one another or separation.

In terms of this invention, the generation of a sound wave and the generated sound wave are referred to collectively as a "sound event." For the sake of clarity, the term "sound event" thus combines the process of exciting an acoustic oscillation and the result of the propagating sound wave produced in this way, since the latter do not directly correspond to one another.

The sound event can extend over a limited chronological tracing. The sound event is preferably an acoustic pulse, impulse, and/or of a temporary nature. The sound event is preferably short, for example shorter than 10, 5 or 2 seconds. It can also be shorter than 1 or 0.5 second.

The sound event generates or is preferably a sound wave with frequencies that are preferably audible and/or can be converted by commercially available microphones into electrical signals, for example between 100 Hz and 20 kHz. Alternatively or in addition, the sound event can generate or be ultrasound, for example between 20 and 200 kHz.

The sound event can be a noise or a tone. For example, the sound event is a clicking, clacking, popping, hissing, buzzing, or beeping.

In terms of this invention, an "acoustic signal" is a sound wave or information corresponding thereto, for example a corresponding electric current or a corresponding electric voltage, a spectrum, or a digital pendant of the sound wave. The acoustic signal can thus be present both as a sound wave and converted in the form of electric current and/or voltage and/or digitized as digital data, wherein the more electric current and/or voltage and/or data correspond to the sound waves or represent the latter. It is not necessary, but preferable, that the acoustic signal is present and processed electrically and/or digitally in the form of digital data, data streams, audio samples or the like.

The acoustic signal has the sound event. This can be done by having the acoustic signal be imprinted by the sound event. It is thus possible for the acoustic signal to be a chronological tracing of a sound wave that the sound event has in the form of a section or onto which the sound event is superimposed in the form of a sound wave. Alternatively or in addition, the acoustic signal is information that corresponds to this sound wave, which information comprises the information originating from the sound event.

The sound event is specific to a property or change in state of the dispensing device. In this way, the sound event preferably makes possible a (clear) identification of the dispensing device or the substance and/or an assignment of the dispensing device to a group or class of dispensing devices or substances. The possible identification of the substance is in this case a property of the dispensing device, since the latter has the substance or is designed for this purpose. Alternatively or in addition, because of specificity, the sound event can make it possible to detect a change in state in the form of a triggering, an actuation, an unlocking, a securing, a substance ejection, or a packing or unpacking.

A sound event is specific to the property or change in state of the dispensing device when the sound event can be different from other sound waves from other sources, and thus the sound event makes possible an assignment or identification.

The term "specific" thus means that the sound event is different from other sound events or can be identified independently of other sound events, preferably so that the sound event can be assigned to the property or change in state of the dispensing device and consequently, by means of the detection of the sound event, the dispensing device, property, or change in state of the dispensing device and/or the substance, or a group or class thereof can be identified. This comprises in particular the detection or differentiation of an event, such as a preparation, dispensing, and/or triggering.

For example, the same type of dispensing devices can be designed by various sound generators to generate different sound events in the case of different substances, in order to differentiate the substances in the case of otherwise identical dispensing devices. In this way, the respective sound event is specific to the substance.

Alternatively or in addition, differently-designed dispensing devices can have sound generators for generating the identical sound event, in order to be able to identify the same substance despite differently-designed dispensing devices.

Also, dispensing devices of the same design or class can have sound generators for generating the same sound event in order to detect the same design or class and/or to generate different sound events in order to be able to distinguish dispensing devices of the same design or class from one another.

The sound generator is designed to generate at least one sound event in the case of the preparation, performing, and/or post-processing of a dispensing of the substance. The generation preferably takes place as a byproduct in the dispensing process.

In terms of this invention, the term "dispensing process" in general combines: the preparation, performing, and/or post-processing of the actual or simulated dispensing of the substance. What are meant in this case are preferably only necessary steps, i.e., those that are absolutely necessary for the dispensing of the substance with proper use of the dispensing device. Such absolutely necessary steps can be for preparing the removal of a packaging or a protective part; for implementing a triggering, without which the dispensing could not be carried out; and/or for post-processing a removal of the dispensing device from the patient and/or a measure that is necessary for reuse.

Preferably, the—or in any case a—sound event is produced in the case of direct dispensing or as a step that directly accompanies the dispensing of the substance. The sound generator is thus designed to generate the sound event in the case of the direct dispensing or a step that directly accompanies the dispensing of the substance. Examples here are the triggering of the dispensing or the phase in which the substance leaves the dispensing device. There can be multiple sound events, however, wherein not all sound events have to be generated with the direct dispensing or a step that directly accompanies the dispensing of the substance.

Also, the system according to the proposed solution has a detection device for checking the acoustic signal in the at least one sound event. Because of this check, the property or change in state of the dispensing device can be detected or assigned, or this is carried out by the detection device.

In particular, the detection device detects or distinguishes the dispensing device, property, or change in state of the dispensing device and/or substance by checking the acoustic signal in the at least one sound event.

In other words, the detection device is thus designed to check and to detect the acoustic signal in the sound event that originates from the dispensing device and that is produced by the sound generator, whether the acoustic signal has the sound event that is specific to the dispensing device, property, or change in state of the dispensing device and/or substance.

The "detection or assignment" of the property or change in state can in principle be or comprise an individual identification of a specific dispensing device or substance or the detection of a dispensing device or substance of a specific group or a type of dispensing devices or substances. The detection of the property of the dispensing device can thus be the detection of the dispensing device as such, but can also consist in that an event is detected with the dispensing device, such as, for example, a direct dispensing, by which conversely, in any case, a dispensing device or group or class thereof and/or substances and in addition a specific state or a specific change in state is/are also detected. By checking the acoustic signal for the at least one sound event, a sound event is preferably detected only when it originates from the dispensing process.

In terms of this invention, a "detection device" is thus first a device that is set up to analyze acoustic signals. It can have, for example, a processor, in particular a signal processor, or other analysis means for processing and evaluating audio signals in order to carry out this range of functions. Also, the detection device is set up specifically for checking. This means that the detection device is suitable optionally based on additional information to distinguish different sound events in the acoustic signal or to detect specific sound events or to distinguish from other sound events.

In order to be able to detect the sound event, the detection device preferably has corresponding information in the form of a sound event pattern. The sound event pattern can also be a signature of the sound event. With this sound event pattern, the detection device can compare the acoustic signal and detect when the sound event appears in the acoustic signal.

The system according to the proposed solution makes it possible in an advantageous way to monitor the dispensing process for dispensing the substance by examining the acoustic signal. It can thus be readily possible to check whether the correct substance is administered and/or whether administration is carried out at all and optionally whether it is carried out correctly, i.e., as specified.

In this case, the detection device can be produced in an especially simple and effective way by a Smartphone or another, in particular portable, device with a microphone and a processor. Specific hardware or expensive implementation of electronics in the dispensing device can thus be avoided. The detection device can have one or more (software) module(s), which can carry out the functions of the detection device.

Also, the check of the acoustic signal and the detection of the sound event make possible many applications that can be implemented by the detection device or made possible externally or in some other way. In one example, the detected or performed dispensing processes are reconciled to a preset value or used in another way to check a provided or preset medication. Alternatively or in addition, the check or the result of the check is used to detect malfunctions or incorrect applications of the dispensing device and optionally to prompt troubleshooting such as error signaling.

For the generation of the specific sound event, in many cases it is sufficient in an advantageous way to modify known dispensing devices not at all, only slightly, or only for certain of the many provided sound events or sound generators specifically for sound generation, so that in the case of the dispensing process, the specific sound event(s) is/are generated.

As a result, the system according to the proposed solution is to be implemented reliably, quickly, easily and with for the most part existing hardware in an unforeseen way and allows universal use, namely especially advantageously in connection with the monitoring of patient compliance (compliance/adherence), operational monitoring, and/or application monitoring.

Another aspect of this invention relates to the detection device for detection of a dispensing process of a preferably pharmaceutical substance that is carried out with a dispensing device of the system by examining an acoustic signal that is generated by a sound generator of the dispensing device for one or more sound events that are specific to the dispensing device and/or the substance.

Another, also independently achievable aspect of this invention relates to a method for monitoring an actual or simulated dispensing of an administrable, preferably pharmaceutical, substance with a dispensing device. In particular, this aspect relates to the detection of dispensing. In this case, an acoustic signal is checked to detect or distinguish the dispensing device, property, or change in state of the dispensing device and/or substance in a sound event that can be generated in a dispensing process comprising the preparation, performing, and/or post-processing of the dispensing with a sound generator of the dispensing device.

Another, also independently achievable aspect of this invention relates to a use of a mobile terminal device for detection of the actual or simulated dispensing of the administrable, preferably pharmaceutical, substance that is carried out with the dispensing device, wherein the mobile terminal device is used to pick up an acoustic signal and to examine it for a sound event that can be generated by the dispensing device during the dispensing process and that is specific to the dispensing device, property, or change in state of the dispensing device and/or the substance.

Another, also independently achievable aspect of this invention relates to a computer program product that has program code means, which, when they are implemented, for example on a processor, implement the method according to the proposed solution for detection. In particular, this is a preferred non-volatile computer-readable storage medium that has instructions, in particular in the form of code, which, when they are implemented on a processor, implement or effect the steps of the method according to the proposed solution.

Another, also independently achievable aspect of this invention relates to a protecting element for a dispensing device for dispensing an administrable, preferably pharmaceutical, substance. Preferably, the protecting element is configured cap-like and/or in the form of a cover or lid. The protecting element has or forms a sound generator which is designed to generate, upon an actual or simulated preparation of a dispensing of the substance, at least one reproducible sound event in an acoustic signal, the sound event being specific to a property and/or change in state of a dispensing device.

The protecting element is preferably configured to generate the sound event upon removing the protecting element from a main body of a dispensing device, wherein the generated sound event is independent of the speed, force and/or other external parameters used for removing the protecting element from the main body. This is conducive to the generation of a reproducible sound event and to a reliable detection of the sound event.

The protecting element preferably has a first part and a second part that are moveable relative to each other between an initial position and an activation position, preferably wherein the initial position and the activation position are different positions of the protecting element. This supports the generation of a reproducible sound event.

The sound generator is preferably configured to generate the sound event after movement of the protecting element from the initial position to the activation position and/or upon return of the protecting element from the activation position to the initial position. This is conducive to a reproducible generation of the sound event.

Another, also independently achievable aspect of this invention relates to a dispensing device for dispensing an administrable substance. The dispensing device has a main body and a protecting element, in particular as configured as described above.

Another, also independently achievable aspect of this invention relates to a system having the dispensing device.

In terms of this invention, substances that are suitable for ingestion by or other administration in a human or animal body are referred to as "administrable substances," which substances can be present in particular in the form of liquids or suspensions—for example, for aerosol formation or injection-tablets, capsules, powders, or granulates.

This invention relates quite preferably to the administration of pharmaceutical substances in the form of medicines, but is not in principle limited thereto. Thus, it is not ruled out that this invention or aspects of the latter can also be advantageous independently of the administration of medicines. In terms of this invention, the term "administrable substance" therefore also comprises, in addition to pharmaceutical agents, substances that can be administered and are not strictly pharmaceutical.

In terms of this invention, "pharmaceutical" substances are pharmaceutical agents or medicines that have an active ingredient for healing or for preventing human or animal diseases. Preferably, in terms of this invention, dietary supplements, in a dosage form that corresponds to that of pharmaceutical agents, are also regarded as being among pharmaceutical substances. Alternatively or in addition, the substance can be cosmetic.

Additional advantages, aspects and properties of the present invention follow from the claims and from the subsequent description of the preferred embodiments with reference to the accompanying drawings.

DETAILED DESCRIPTION OF THE INVENTION

In the Figures, the same or similar parts are identified with the same or similar reference numbers and may have similar advantages, properties, and actions, even if a description is not repeated. Furthermore, reference is made to the definitions and statements that are cited in the parts of the general description.

Figure 1:
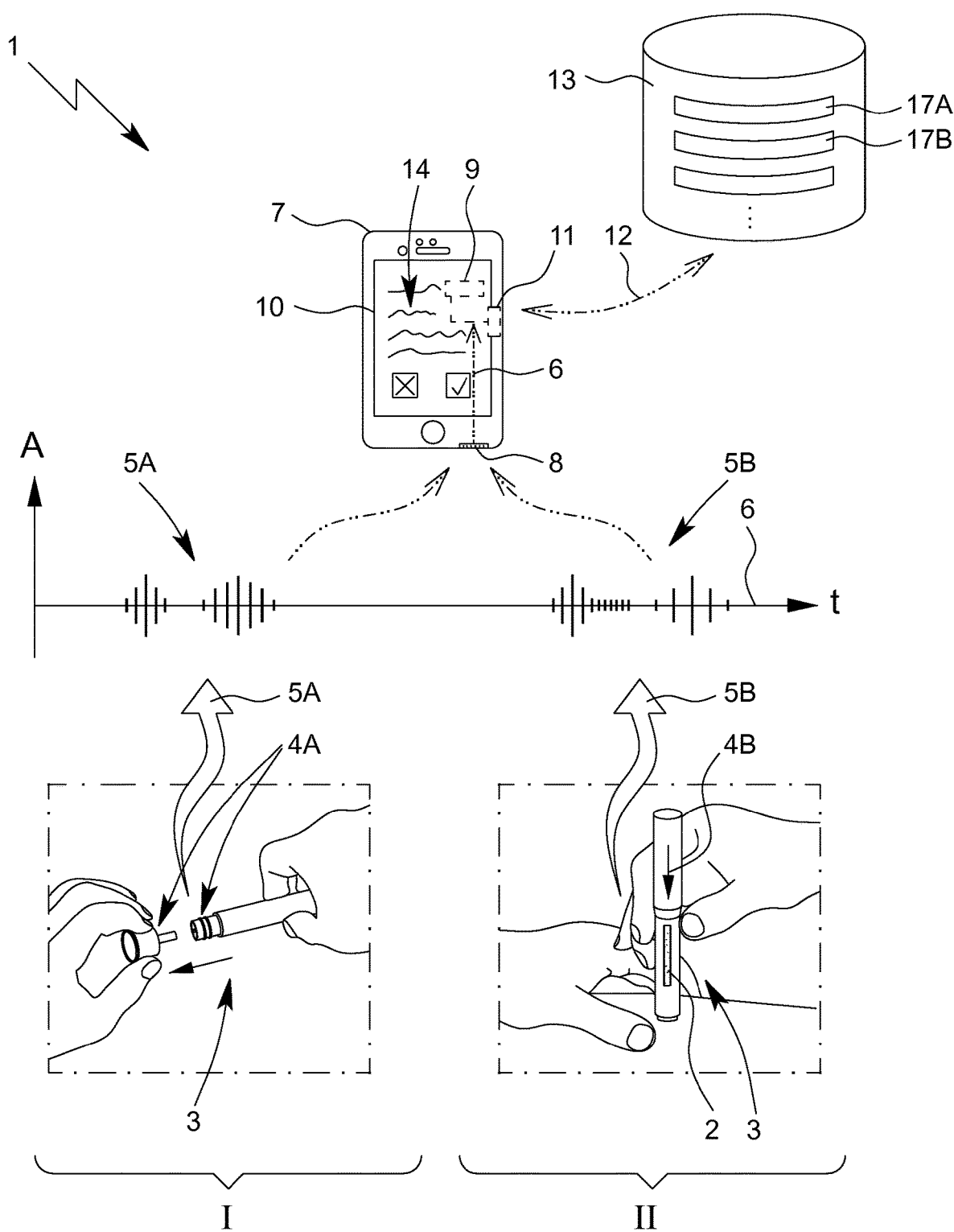
FIG. 1 shows a system according to the proposed solution.

FIG. 1 shows a system 1 according to the proposed solution for acoustic monitoring of a preparation, performing, and/or post-processing of a dispensing of an administrable, preferably pharmaceutical, substance 2.

The system 1 has a dispensing device 3 for dispensing the substance 2. The dispensing device 3 in turn has a sound generator 4 for generating at least one sound event 5 that is specific to a property or change in state of the dispensing device 3 in an acoustic signal 6 in the case of the preparation, performing, and/or post-processing of a dispensing of the substance 2.

The preparation, performing, and/or post-processing is/are also referred to below as a dispensing process. However, the phase in which the substance 2 leaves the dispensing system 3 is called (direct) dispensing.

Also, the system 1 preferably has a detection device 7 for checking the acoustic signal 6 for the at least one sound event 5A-5E in order to make possible a detection of the property or change in state of the dispensing device 3. The detection device 7 is preferably designed for detecting or distinguishing the dispensing device 3, property, or change in state of the dispensing device 3 and/or substance 2 by checking the acoustic signal 6 for the at least one sound event 5.

In the example according to FIG. 1, the dispensing device 3 is a so-called autoinjector. In principle, the invention, as it is explained in more detail below based on this autoinjector, can however, be applied in a corresponding way to other dispensing devices 3.

Figure 2A:
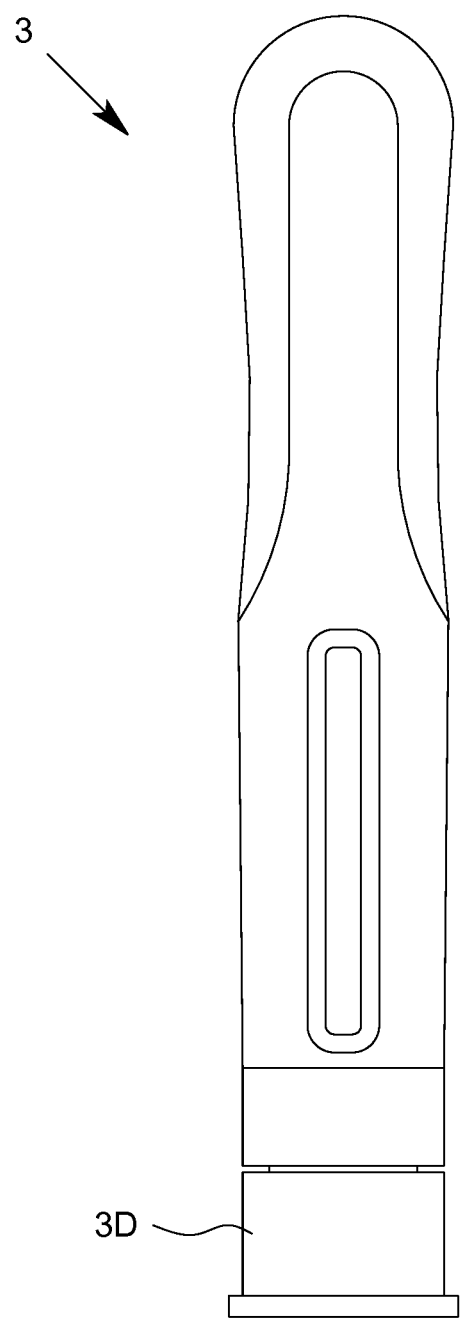
FIG. 2A shows a view of a dispensing device of the system according to the proposed solution from FIG. 1.
Figure 2B:
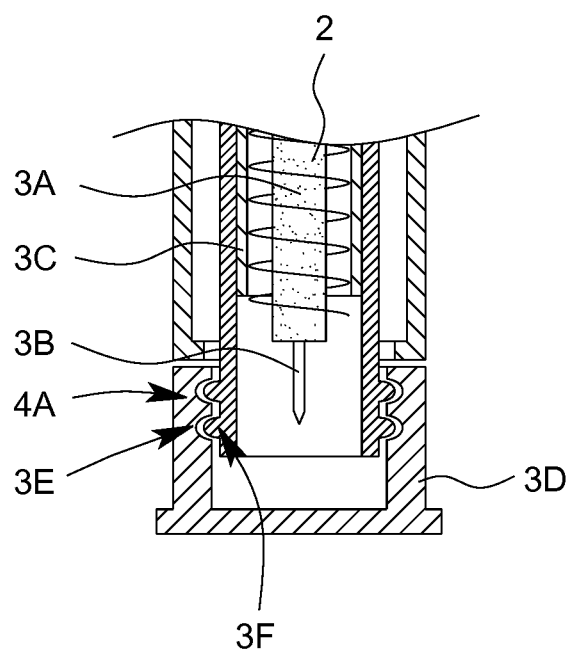
FIG. 2B shows a partial section of the dispensing device according to FIG. 2A.
Figure 3:
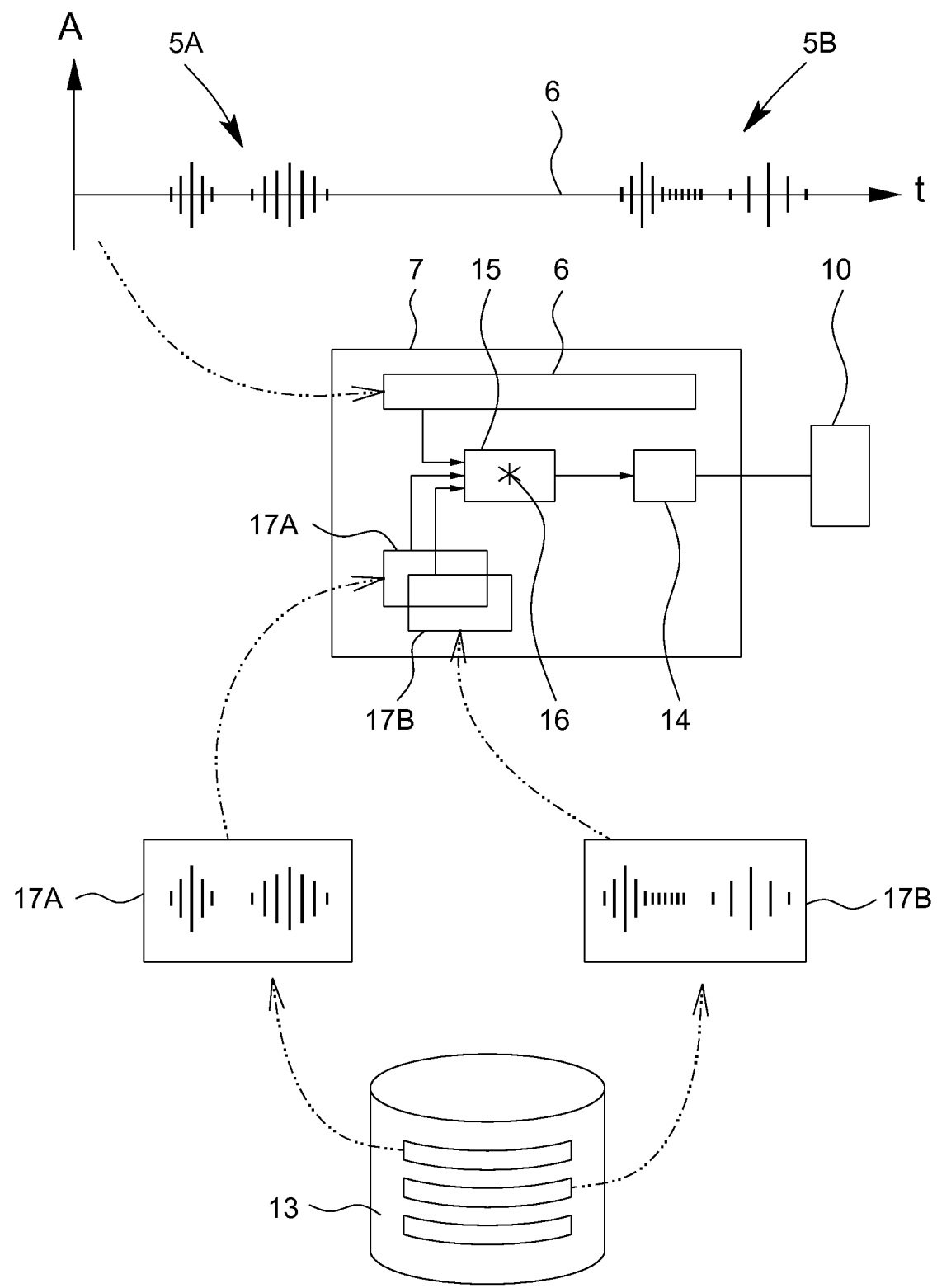
FIG. 3 shows a schematic view of the detection device.

FIG. 2A shows a view of the dispensing device 3, which is present by way of example in the form of an autoinjector, while FIG. 2B shows a partial section of the dispensing device 3 from FIG. 2A.

The dispensing device 3 has, as indicated in section according to FIG. 2B, at least one administrable dose of the substance 2, here a carpule 3A that is filled with the substance 2 and with an injection needle 3B.

The dispensing device 3 can be triggered, whereupon the substance 2 is administered. To this end, the carpule 3A with the injection needle 3B is moved in a sudden manner from the dispensing device 3 in order to penetrate into the tissue of a patient and to inject the contents of the carpule 3A, i.e., the substance 2, by means of the injection needle 3B.

To trigger the dispensing, an actuator 3C is provided at the dispensing device 3. In this illustrative example, the actuator 3C is a tube section or a sleeve that is pushed into the dispensing device 3 for triggering when the dispensing device 3 is attached to the patient and in this way brings about the triggering process, which causes the carpule 3A to move and the substance 2 to be administered. In the case of other dispensing devices 3, the actuator 3C can also be implemented differently, however.

The triggering is prevented by a protecting element 3D in the initial state of the dispensing device 3. The protecting element 3D in this example is a cap, which prevents the triggering and/or dispensing of the substance 2.

Alternatively or in addition, however, other protecting elements 3D can also be provided, which prevent the dispensing or triggering in an initial state of the dispensing device 3. The protecting element 3D can be unlocked in order to make possible the subsequent triggering and/or dispensing. In the illustrative example, the protecting element 3D in the form of the cap is removed, and only when or as soon as the protecting element 3D is removed can the triggering take place.

It is preferred that the protecting element 3D of the dispensing device 3 has or forms the—or one of the—sound generator(s) 4A. In this case, the protecting element 3D can keep the substance 3 from being dispensed in an initial state and with generation of the sound event 5A can be transferred into an enabling state for enabling the dispensing of the substance 2.

The protecting element 3D together with the part of the dispensing system 3 on which the protecting element 3D is arranged in the initial state (locked, pushed-on cap) forms the sound generator 4A here. In the illustrative example, the cap forms the sound generator 4A in such a way that it forms a cylinder-piston unit with the other dispensing device 3, by which when removing or opening the cap, an underpressure is generated in a hollow space that is formed by the cap. With complete removal or opening (enabling state), ambient air flows into this hollow space, by which the plop noise known for the opening or removal of a cap is generated.

The sound generator 4A is preferably a structure that is not required for the dispensing process or the dispensing, not directly involved in the dispensing, and/or specifically designed or modified for the generation of the sound event 5A.

In this example, the sound generator 4A is a structure of the dispensing device 3 that is specific to or modified for sound generation, which device is designed to generate a sound event 5A that is specific to the dispensing device 3, property, or change in state of the dispensing device 3 and/or the substance 2.

In this example, the sound generator 4A has surface structures 3E and counter-structures 3F or is formed in this way, which structures are designed optionally for the dispensing process and specifically for this purpose to generate or to modify the sound during operation, i.e., the sound event 5A that is produced by the sound generator 4A in a way that is specific to the dispensing device 3, property, or change in state of the dispensing device 3 and/or the substance 2.

In the example, the protecting element 3D (an inside wall of the cap) has a surface structure 3E that interacts with a counter-structure 3F of the dispensing device 3 in such a way that during unlocking, here, i.e., removing or opening the cap, a sound event 5A is generated or changed. The surface structure 3E with the counter-structure 3F forms the sound generator 4A or a part thereof.

Here, by way of example, ribs, beads, or grooves that engage in one another are provided. When the cap is removed, these lead to an oscillation of the protecting element 3D or the housing of the dispensing device 3 and consequently to a sound wave as a sound event 5A that is produced by this oscillation and that corresponds to the latter.

This sound wave, produced by the modified structure, precedes the plop noise in the example and may partially overlap the latter.

In this way or a similar way, a specific sound event 5A can be brought about by a specific or modified structure, and various sound events 5A can be brought about by various possible configurations of the surface structures and counter-structures 3E, 3F, even when the dispensing device 3 can be identical relative to its design that relates to the dispensing.

In any case, it is not necessary, however, that the sound generator(s) 4A has/have a modified structure in order to generate the specific sound event 5A. It can be sufficient, in particular for identification of a group or class of dispensing devices 3 or for the identification of a dispensing herewith, to monitor or to detect sound events 5A that accompany the dispensing process, without an existing dispensing device 3 being modified for this purpose. Sound generators 4A are then the existing structures that generate sound in the case of the dispensing process. The sound events 5A can be specific enough for a detection, in particular in the case of more complex dispensing devices 3.

The sound generator 4A, 4B can thus be either a structure of the dispensing device 3 that is already existing or prepared or necessary for the dispensing of the substance 2 or it can be specifically formed or modified for this purpose.

The sound generator(s) 4A is or are preferably designed so that the sound event 5A or the sound events 5A in the dispensing process is or are generated necessarily and in a reproducible manner.

In the illustrative example, this is achieved in such a way that the sound generator 4A that made the protecting element 3D must be unlocked (removed) before triggering can take place, by which the sound event 5A is generated.

The necessary generation of the sound event 5A can also be implemented in some other way, however. For example, a triggering mechanism can form a sound generator 4B, so that the sound event 5B is necessarily generated with the triggering (cf. FIG. 1).

For the sound generator 4B of the triggering mechanism and additional or different sound generators 4A, 4B, the features and properties that are explained in connection with the sound generator 4A of the protecting element 3D correspondingly apply unless otherwise described or the contrary follows from the context.

In principle, the sound generator 4A, 4B can be based on various measures for sound generation. In particular, the sound generator 4A, 4B can be or can have a ratchet, flapper, vibrating bell, rattle, whistle or structure for generating a reproducible plopping, clacking, clicking, screeching, clattering, grinding, rattling, hissing, squeaking, buzzing, whistling or can be or can have oscillations caused by a stick-slip effect.

For example, because of the movable parts, which move along on a sound generator 4B in the form of a ratchet, produced by the triggering, the dispensing device 3 can generate a clattering as a sound event 5B. In a corresponding way, another specific sound event 5B can be produced by or during performing the dispensing of the substance 2 with another sound generator 4B.

In one aspect of this invention, the dispensing device 3 has at least two different sound generators 4A, 4B. These are preferably designed such that in various phases of the dispensing process that follow one another in time, a first sound event 5A and, preferably chronologically spaced, a second-preferably different from the first-sound event 5B are generated.

In one aspect of this invention, the dispensing device 3 has multiple sound generators 4A, 4B or a sequence system with multiple sound generators 4A, 4B for generating a sequence of at least or more than two sound events 5A, 5B that (necessarily) follow one another in time during the course of the dispensing process. In this way, the acoustic signal 6 is imprinted by the sequence.

A sequence system can first consist of two or more sound generators 4A, 4B or have the latter. Also, it is preferable that the sequence system or the dispensing device 3 is coupled to the latter in such a way that the sound generators 4A, 4B during the dispensing process generate sound events 5A, 5B in a specific sequence. In this case, the sequence system is not necessarily a separate system, but rather it can also be produced by the design of the dispensing device 3 or by its components.

In the illustrative example, the dispensing device 3 is designed so that first, a first sound event 5A is generated with the first sound generator 4A of the protecting element 3D, before a subsequent second sound event 5B is or can be generated by the second sound generator 4B of the triggering mechanism, which then form such a sequence. The dispensing device 3 in this case implements the sequence system by design. Alternatively, however, a sequence system can also be a separate component. Furthermore, there are also other possibilities to generate a sequence with more than two sound events 5A, 5B or to provide sound generators 4A, 4B for this purpose in the case of the dispensing device 3.

In another aspect, the system 1 preferably has multiple dispensing devices 3, which are distinguished relative to the substance 2 and the sound generator 4A, 4B and otherwise are designed identically or similarly. In this way, the same acoustic signal 6 can be generated by dispensing devices 3 with the same properties relative to the substance 2. Furthermore, different sound generators 4A, 4B or acoustic signals 6 can be generated by dispensing devices 3 with various properties relative to the substance 2. This makes possible the differentiation of various substances 2 themselves in the case of otherwise at least essentially identical dispensing devices 3.

It is preferred that the sound generator(s) 4A, 4B generate(s) the sound event(s) 5A, 5B in the dispensing process necessarily and in a reproducible manner in a specific sequence. Here, this is ensured for the first sound event 5A in such a way that the protecting element 3D has to be removed or unlocked before the dispensing of the substance 2 can be carried out. Moreover, this is ensured for the second sound event 5B in such a way that the second sound event 5B is produced by the triggering of the dispensing as such a one; the dispensing of the substance 2 thus necessarily accompanies the generation of the second sound event 5B by the second sound generator 4B. There are, however, also other possibilities for implementing such necessary and reproducible sequences of sound events 5A, 5B in the dispensing process.

An also independently achievable aspect of this invention relates to the detection of a dispensing of an administrable, preferably pharmaceutical, substance 2 that is carried out or simulated with a dispensing device 3. In this case, an acoustic signal 6 is examined for a sound event 5A in the acoustic signal 6 that is specific to the dispensing device 3, property, or change in state of the dispensing device 3 and/or the substance 2.

The sound event 5A, 5B for which the acoustic signal 6 is examined is specific to or characteristic of the dispensing device 3, property, or change in state of the dispensing device 3 and/or substance 2 and in particular of the preparation, performing, and/or post-processing of the dispensing of the substance 2 or the dispensing process of the substance 2 by means of the dispensing device 3. The sound event 5A, 5B is preferably generated in this dispensing process. The sound event 5A, 5B is preferably specific to or characteristic of the dispensing process or a step in the latter.

By examining the acoustic signal 6 for the at least one sound event 5A, 5B, the dispensing device 3, property, or change in state of the dispensing device 3 and/or the substance 2 can consequently be detected or distinguished. This includes the detection or differentiation of groups or classes of dispensing devices 3 or substances 2.

An example of the detection of the dispensing device 3, property, or change in state of the dispensing device 3, and/or the substance 2 by checking the acoustic signal 6 for the at least one sound event 5A, 5B is explained in more detail below based on FIG. 1.

In a Phase I, the dispensing device 3 is prepared for triggering by the dispensing device 3 being unlocked with the protecting element 3D. This preparation or unlocking of the protecting element 3D, in this example the removal of the cap, generates a first sound event 5A. In the illustrative example, the protecting element 3D is provided to this end with the sound generator 4A, which is designed and set up to generate the sound event 5A during unlocking (removal of the cap).

The sound event 5A is represented in the acoustic signal 6 by (indicated) acoustic oscillations. The sound event 5A moves into the acoustic signal 6 in such a way that the sound generator 4A generates a sound wave, which forms a part of the acoustic signal 6.

In the illustrative example, the dispensing device 3 has the protecting element 3D as a first sound generator 4A, which element is preferably designed cap-like and generates a plop noise during unlocking, i.e., in the case of the preparation of the dispensing of the substance 2. As already previously explained, the protecting element 3D can be especially set up or modified optionally and preferably for generating a specific sound event 5A, here a modified plop noise.

In Phase II according to FIG. 1, the dispensing device 3 is triggered, which in turn leads to a sound event 5B, which is represented in the acoustic signal 6 by indicated acoustic oscillations. In this example, the dispensing device 3 that is designed as an autoinjector is triggered by attaching to a patient with the actuator 3C or in another way. The triggering and/or direct dispensing of the substance 2 in this case produces the sound event 5B.

For generating the second sound event 4B, the dispensing device 3 has a second sound generator 4B, which is implemented here by the triggering mechanism of the dispensing device 3. This triggering mechanism generates a clacking, followed by a softer continuous noise and an optional clacking at the end of the injection process.

In its chronological tracing, the acoustic signal 6 therefore contains multiple different sound events 5, which in this example originate, on the one hand, from the preparation and, on the other hand, from the performing of the (direct) dispensing of the substance 2 with the dispensing device 3.

The acoustic signal 6 can also have other sound events 5A, 5B, however, which do not originate from the dispensing system 3 or from other steps. The latter can be ignored and/or discarded and/or identified as features for exclusion.

The acoustic signal 6 is picked up and processed by the detection device 7. The detection device 7 can be implemented and is advantageous in the system 1 as well as independently of the system 1 and other parts of the system 1. It therefore represents a separate aspect of this invention.

The detection device 7 is designed to detect the property or change in state of the dispensing device 3 or the dispensing device 3 and/or substance 2 in such a way that the acoustic signal 6 is examined by the detection device 7 for one or more sound events 5A, 5B that is/are generated by at least one sound generator 4 of the dispensing device 2 and is/are specific to the property or change in state of the dispensing device 3 or to the dispensing device 3 and/or the substance 2.

The detection device 7 determines the property or change in state of the dispensing device 3 or the dispensing device 3 and/or substance 2 preferably in the case of detecting at least one sound event 5A, 5B in the acoustic signal 6 based on the detected sound event 5A, 5B.

The detection device 7 preferably has a microphone 8, via which the acoustic signal 6 is picked up with the sound events 5A, 5B.

Furthermore, the detection device 7 preferably has a processor 9 for administering the acoustic signal 6. In particular, the processor 9 is a signal processor—also called a digital signal processor (DSP)—or it has such a one. In this case, this is a processor 9 or a part thereof with computing structures that are especially suitable or are designed to process audio signals. The use of a signal processor has proven especially advantageous since the latter especially efficiently and effectively processes the acoustic signal 6, in particular when it continuously monitors a continuous acoustic signal 6.

The detection device 7 preferably digitizes the acoustic signal 6 and processes it digitally. The detection device 7 can to this end have an analog-digital converter (ADC) in order to convert an acoustic signal 6, which is converted by the microphone 8 into analog electrical signals 6, into a digital acoustic signal 6. In principle, however, an analog processing is also possible.

The detection device 7 detects or distinguishes the dispensing device 3 and/or the substance 2 by preferably continuous checking of the acoustic signal 6 for the at least one sound event 5A, 5B. It is thus preferred that the signal 6 is checked without interruption over an extended period in order to identify sound events 5A, 5B in the acoustic signal 6.

The detection device 7 can optionally have an output device 10 for outputting a result of the checking of the acoustic signal 6 or for signaling the detection or differentiation or a characteristic value of this. The output device 10 can be or have a display, a loudspeaker, and/or another user interface.

In another aspect of this invention, the detection device 7 has an interface 11 for producing a data link 12, for example to a database 13. The database 13 can form part of the system 1 or be provided separately therefrom as an external database 13.

The detection device 7 is especially preferably designed for detecting or distinguishing at least two preferably different sound events 5A, 5B that in each case are specific to the dispensing device 3 and/or the substance 2. This is done by checking the acoustic signal 6 for these sound events 5A, 5B.

Preferably, the detection device 7 has an analysis device 15 for examining the different sound events 5A, 5B, detected in checking, for a predetermined sequence or order, or forms such an analysis device 10.

The detection device 7 is preferably designed to output a result 14 via the output device 10 when the determined order of various sound events 5A, 5B that is specific to or characteristic of the dispensing process has been detected by the detection device 7 or analysis device or to output an error, when an order, amount, or number of different sound events 5A, 5B that deviates therefrom has been detected.

Especially preferably, the detection device 7 is designed to distinguish between different sound events 5A, 5B of the same, similar or different dispensing devices 3.

For detection, the detection device 7 can be designed for comparison of the acoustic signal 6 with one or more sound event patterns 17A, 17B.

Sound event patterns 17A, 17B can be present as so-called audio samples, which have information relative to sound events 5A, 5B. In this case, these are segments of an acoustic signal 6 that (in each case) have one or more sound events 5A, 5B that took place in the past, were forecast, simulated or in another way suitable for comparison to the signal 6. Sound event patterns 17A, 17B are similar in particular to the sound events 5 for which the acoustic signal 6 is to be examined or correspond to the latter. Alternatively or in addition, these are one or more sound events 5A, 5B representing information or information derived therefrom, such as processed, compressed, or aggregated sound events 5. These include spectra and/or statistical information on sound events 5.

The sound event pattern(s) 17A, 17B can have assignment means. With these assignment means, an assignment of the sound event pattern 17A, 17B or the sound event 5A, 5B that corresponds thereto to the dispensing device 3, the property, and/or the change in state of the dispensing device 3 or substance 2 can be carried out. The sound event pattern 17A, 17B or assignment means is thus preferably designed for this purpose or contains information relative to the assignment. The assignment can be carried out by the detection device 7. It is sufficient when the assignment means are related, linked, and/or (logically) associated with the respective sound event patterns 17A, 17B, so that the sound event patterns 17A, 17B have the assignment means.

The detection device 7 preferably has one or more of the sound event patterns 17A, 17B. Alternatively or in addition, one or more of the sound event patterns 17A, 17B is/are stored in the database 13 and can be accessed from the latter by the detection device 7.

The sound event pattern(s) 17A, 17B is/are used to detect corresponding sound events 5A, 5B in the signal 6. To this end, the detection device 7 compares the sound event pattern 17A, 17B to the signal 6. When a sound event 5A, 5B can be detected in the signal 6 by means of a sound event pattern 17A, 17B, this can be recorded as a result 14.

When multiple sound events 5A, 5B are detected in the signal 6 by means of the same sound event patterns 17A, 17B, the latter can be recorded as one or more results 14.

When multiple sound events 5A, 5B are detected in the signal 6 by means of multiple sound event patterns 17A, 17B, the latter can be recorded as one or more results 14.

The results 14 can be output by the detection device 7 via the output device 10, further processed, and/or conveyed.

The detection device 7 preferably has a correlation module 16 for generating a correlation of the acoustic signal 6 with one or more sound event patterns 17A, 17B. The correlation can be done continuously and/or by a mathematical folding in the time range or multiplication in the frequency range, the latter preferably based on a (Fourier-) transformed signal 6. The correlation is a preferred method for comparison of the sound event pattern 17A, 17B to the signal 6.

The detection device 7 is preferably designed to output a result 14 when it detects that the acoustic signal 6 is impressed by a sequence of sound events 5A, 5B that follow one another in time, which sequence corresponds to the course of steps of the dispensing process, and which sequence thus has corresponding sound events 5A, 5B. Alternatively or in addition, the detection device 7 preferably is designed to output an error when it detects that the acoustic signal 6 is not impressed by a sequence of sound events 5A, 5B that follow one another in time, which sequence corresponds to the course of steps of the dispensing process, and which sequence thus has corresponding sound events 5A, 5B. In this way, the function and/or medication can advantageously be ensured or can be improved relative to the reliability.

The detection device 7 preferably detects dispensing processes with the dispensing system 3 or by the substance 2. This can be carried out by detection of the dispensing system 3 or by the substance 2 or based on this detection.

The detection device 7 can have a counter that counts the number of dispensing cycles or dispensing processes with the dispensing device 3.

Alternatively or in addition, the detection device 7 is designed for comparison of detected dispensing processes to a preset value. On this basis, optionally additional measures can be automatically set up, for example a signaling or transmission of information.

Further processing of the results 14 can preferably be carried out by the detection device 7 or externally, so that patient compliance (compliance/adherence) can be supported or controlled. To this end, based on one or more results 14, information or warnings can be output. Alternatively or in addition, one or more results 14 or indicators derived therefrom can be forwarded, for example to a medical practitioner, a medical system, or the like.

Another, also independently achievable aspect of this invention relates to the use of a mobile terminal device, preferably a Smartphone, a tablet computer, and/or wearable devices, in particular a Smartwatch or fitness arm band, as a detection device 7 or for detection of dispensing, performed with a dispensing device 3, of an administrable, preferably pharmaceutical, substance 2 or the detection of a simulation of such dispensing.

In this case, the mobile terminal device is used in order to pick up the acoustic signal 6 and to examine it for a (characteristic) sound event 5A, 5B that is generated by the dispensing device 3 during the preparation, performing, or post-processing of the dispensing of the substance 2 and that is specific to the dispensing device 3, property, or change in state of the dispensing device 3 and/or the substance 2, or the dispensing process.

In an also independently achievable aspect, this invention also relates to a computer program product that has program code means that, when they are implemented, perform the method according to the proposed solution. In particular, the computer program product is a computer-readable-preferably non-volatile-storage medium, having instructions that, when they are implemented on a processor 9, effect the method according to the proposed solution or an implementation of the steps of the method according to the proposed solution. This can be a storage device of the detection device or a storage device that is separate therefrom.

The invention was explained based on the preferred example of a dispensing device 3 in the form of an autoinjector. However, additional dispensing systems 3, sound generators 4A, 4B, and/or sound events 5A, 5B are possible, so that below, additional examples based on FIGS. 4 to 7 are explained.

Figure 4:
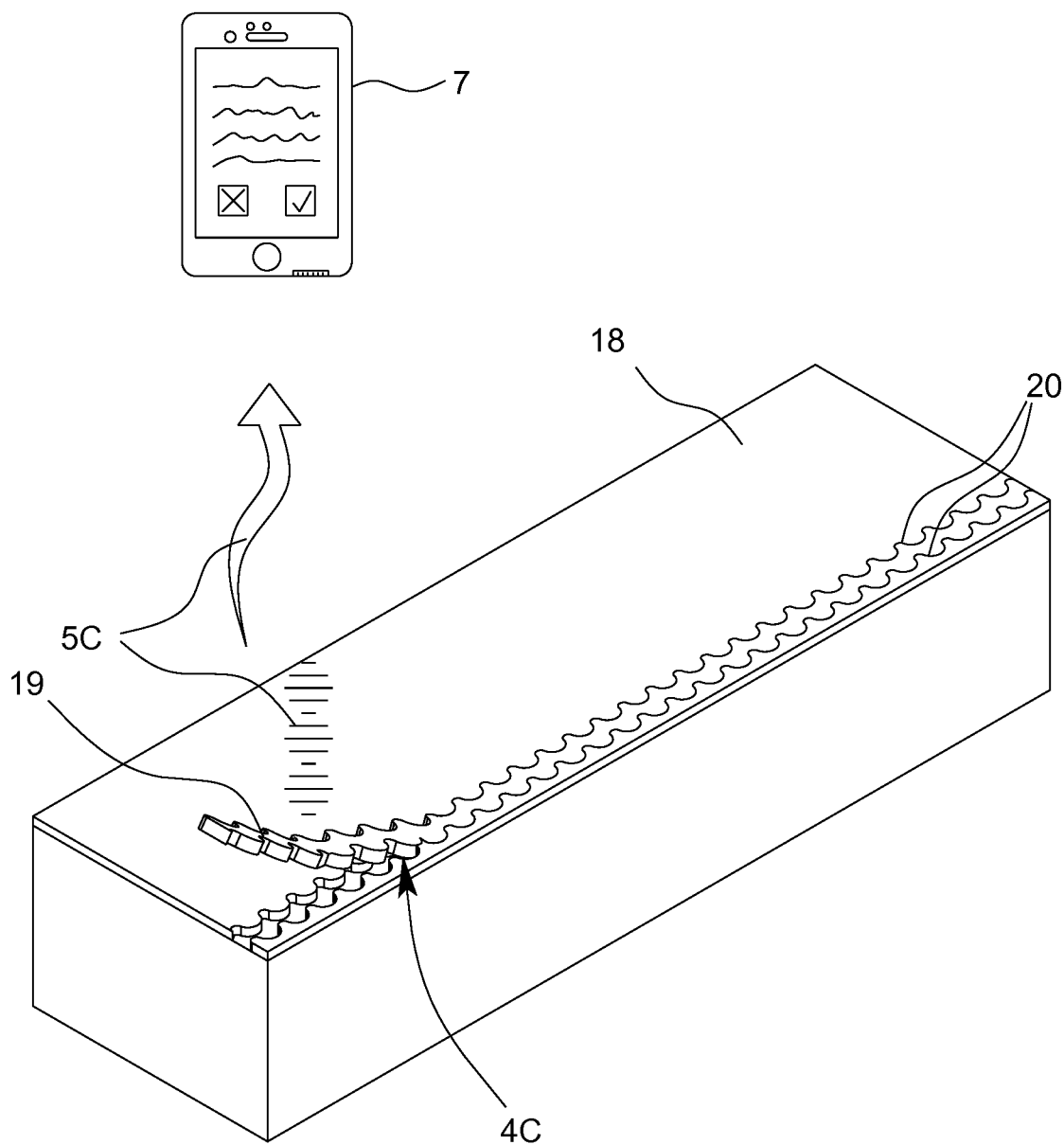
FIG. 4 shows the system according to the proposed solution according to FIG. 1 with a packaged dispensing system.

FIG. 4 shows a secondary packaging 18. This is present in the example as a covering box. The secondary packaging 18 can be separated by means of a tear flap 19 or along one or more predetermined scoring lines 20. In this case, the secondary packaging generates a sound event 5C. The tear flap 19 or predetermined scoring lines 20 therefore form a sound generator 4C.

The sound generator 4C is preferably designed to generate a sound event 5C that is specific to or characteristic of the dispensing device 3, the property, or change in state of the latter, or the substance 2.

The specificity of the sound event 5C, i.e., the suitability of the sound event 5C for distinguishing the packaged dispensing device 3 from other dispensing devices 3, can be improved in such a way that the sound generator 4C is changed/modified compared to the usual tear flaps 19 or predetermined scoring lines 20.

It is thus possible to provide a specific or particular, preferably irregular fluting or toothing, for example a fluting or toothing at variable distances—in particular periodic—of individual flutes or teeth or groups thereof, as indicated in the illustrative example, which leads to the specific sound event 5C.

Figure 5:
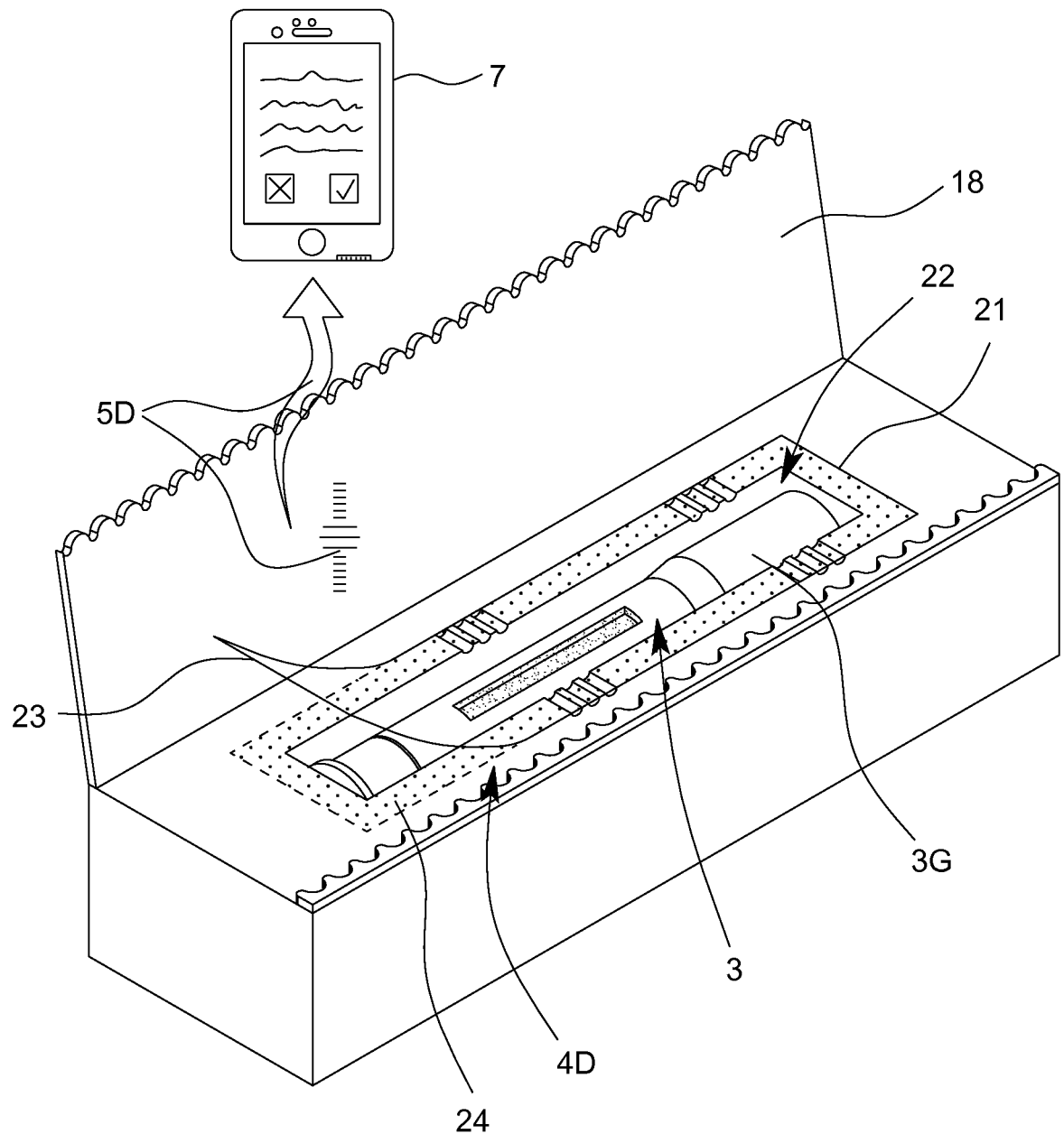
FIG. 5 shows the system according to the proposed solution according to FIG. 4 with open packaging.

FIG. 5 shows a primary packaging 21, in which the dispensing device 3 is directly arranged. In the illustrative example, the primary packaging 21 is a blister that has a receptacle 22, into which the dispensing device 3 is inserted and is enclosed by means of a film 23 by reversible edge-side adhesive 24.

The film 23 can be pulled off for removal from the dispensing device 3. The film 23 in this case forms a sound generator 4D. In this respect, the film 23 generates a specific noise as a sound event 5D during the removal from the receptacle 22.

In general, the structure of the sound generator 4D-here, i.e., that of the blister, the receptacle 22, the film 23 and/or the adhesive 24—is preferably designed such that over the course of the process that generates the sound event 5D, here the tearing, the generation of the sound event 5D is variable in such a way that the sound event 5D that can be generated or is generated is or will be changed or modified accordingly throughout. In this way, the sound event 5D can be especially specific or characteristic.

Alternatively or in addition, the sound event 5D can contain and transport identification information. Consequently, a detection or differentiation can be carried out in an especially reliable manner by means of the identification information. Corresponding measures are also possible in the case of other sound generators 4A-4D. This can also be achieved by a sound generator 4A-4D, which generates a variable sound event 5A-5D, so that by the variability or changing, in particular modulation, data are integrated into the sound event 5A-5D.

In the described way and not limited to the concrete embodiment, the sound generator 4A-4D can thus be designed to acoustically modulate identification information or other information that preferably pertains to the dispensing device 3 and/or substance 2 in the sound event 5A-5D. This leads to a type of melody or chord progression or progression of various noises, by which the identification information or other information is converted from the structure of the sound generator 4A-4D into the sound event 5A-5D. In the example from FIG. 4 or else in general, this can be carried out by a toothing or topography that is varied over the course of the tear flap 19 or predetermined scoring lines 20 or other surface structure 3E or counter-structure 3F.

Based on the modulated sound event 5D, the detection device 7 can then implement a detection or differentiation of the dispensing device 3, property, or change in state of the dispensing device 3 and/or the substance 2, and namely especially in a reliable, specific, and/or differentiated manner.

In this way-preferably by the detection device 7-a sound event pattern 17A, 17B can be compared to the acoustic signal 6, which corresponds to the sound event 5D with the modulated (identification) information. When the sound event 5D with the (identification) information is subsequently detected, the dispensing device 3, the property, the change in state of the latter, and/or the substance 2 is or will be detected or makes this possible.

Alternatively or in addition, multiple sound event patterns 17A, 17B can be provided for various modulated parts of the sound event 5D and can be used to differentiate the various modulated parts of the sound event 5D. The results 14 or series of results 14 can then be used for demodulation of the (identification) information.

The (identification) information can thus be recovered from the sound event 5D and can be used for especially reliable, individual, and/or differentiated detection or differentiation of the dispensing device 3, property, or change in state of the dispensing device 3 and/or the substance 2.

Preferably, the detection device 7 is correspondingly designed to demodulate information that is modulated onto a sound event 5D, in order to prepare an improved detection or differentiation of the dispensing device 3, property, or change in state of the dispensing device 3 and/or of the substance 2. To this end, the detection device 7 preferably has a demodulator for demodulation of the acoustic signal 6 for the purpose of recovering (identification) information that is modulated to this signal 6 or to one or more sound events 5A-5D in the signal 6.

In another, also independently achievable aspect, the dispensing device 3 can have a device 3G for changing sound events 5A-D. In the illustrative example according to FIG. 5, the device 3G is a grip part or other device 3G that can be applied to the dispensing device 3 or its packaging. The device 3G can be applied subsequently to the dispensing device 3. In particular, it can be plugged in.

The device 3G changes the property of one or more sound generators 4 of the dispensing device 3 in such a way that the sound generator(s) 4 generate(s) sound events 5A-D that can be distinguished with and without the device 3G or with different devices 3G or is/are designed for this purpose. In particular, sound events 5A-D are modified in such a way that a natural resonant frequency or a resonant element of the dispensing device 3 or packaging, a damping or general oscillating properties of the dispensing device 3 are changed.

With the device 3G for changing sound events 5A-D, it is possible to individualize sound events 5A-D. In this way, dispensing devices 3 can subsequently also be made distinguishable from one another. Thus, for example, with different devices 3G, otherwise identical dispensing systems 3 can be made distinguishable with respect to different substances 2.

Figure 6:
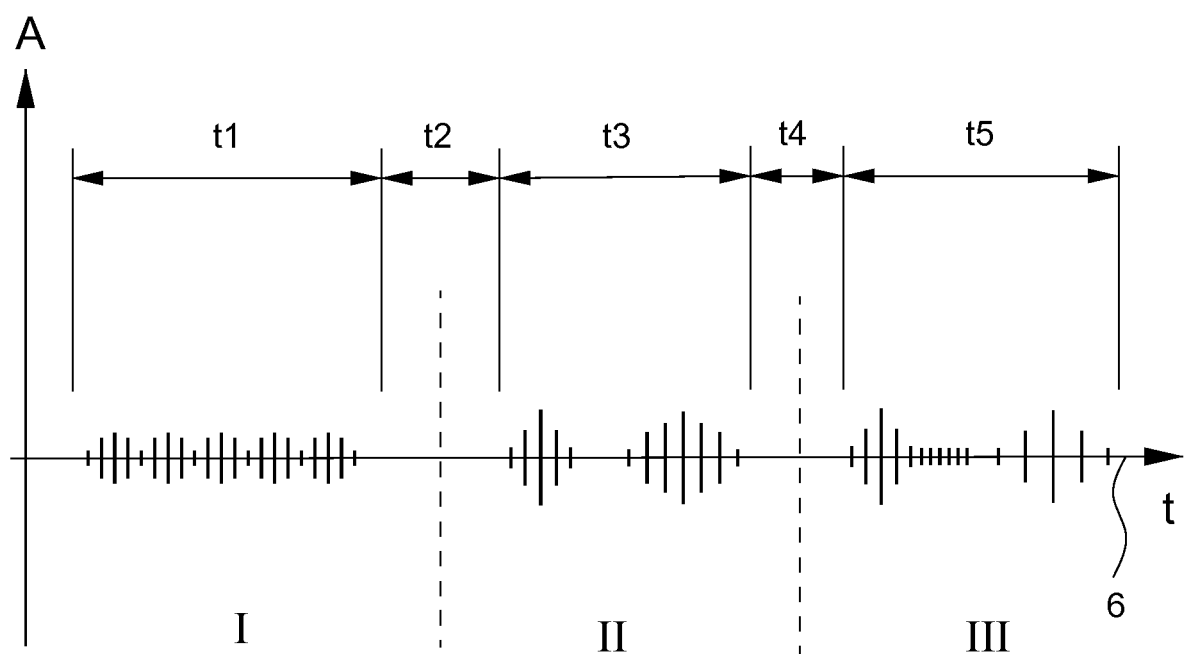
FIG. 6 shows the chronological tracing of an acoustic signal, as it can be produced with the system according to the proposed solution with a packaged dispensing device by the dispensing process.

FIG. 6 shows a series of sound events 5A-D in the signal 6 in three Phases I, II, and III that follow one another chronologically.

In the first Phase I, the signal 6 in a first time span t1 has the sound event 5C, which is produced by the sound generator 4C of the secondary packaging 18.

In Phase II, after a down time t2 in which the primary packaging 21 is removed, in a time span t3, the signal 6 has the first sound event 5A, which originates from the unlocking of the dispensing device 3 by means of the protecting element 3D.

In Phase III, after another down time t4, in which the dispensing system 3 is moved to the dispensing point, in a time span t5, the signal 6 has the second sound event 5B, which originates from the sound generator 4B of the actuator 3C.

The signal can be checked by the detection device 7 for detecting or distinguishing the dispensing device 3, property, or change in state of the dispensing device 3 and/or the substance 2 by examining the acoustic signal 6 for at least one of the sound events 5A-D.

It is thus possible for the check to be limited to the second sound event 5B, which is detected in Phase III. This sound event 5B can be specific or characteristic enough in particular to detect the dispensing device 3 as belonging to a group and/or to detect a dispensing of the substance 2 with this dispensing device 3.

Alternatively, the signal 6 can be checked for at least two sound events 5A-D. When a check is performed for the first sound event 5A and the second sound event 5B, and both sound events 5A, 5B in Phases II and III are detected, then, in addition to the findings from the detection of only the second sound event 5B, it is possible to detect that the dispensing device 3 has been prepared for dispensing, namely by removing the protective part 3D.

When the check is performed for the sound event 5C that originates from the sound generator 4C of the secondary packaging, it can be detected alternatively or in addition whether the dispensing system 3 has been removed from the secondary packaging 18 as expected.

When the check is performed for the sound event 5D that originates from the sound generator 4D of the primary packaging 21, it can be detected alternatively or in addition whether the dispensing system 3 has been removed from the primary packaging 21 as expected. This is not the case in the example.

The signal 6 is preferably checked for at least two, especially preferably at least or exactly three sound events 5A, 5B, 5C/5D, namely the unpacking, the unlocking and the triggering. Thus, when all sound events 5A, 5B, 5C/5D in the signal 6 are detected (by the detection device 7), it can be inferred that a properly-prepared originally-packaged dispensing device 3 has been triggered, and a direct dispensing, optionally dispensing with which substance 2, has taken place.

Preferably, the series of the sound events 5A-5D is checked (by the detection device 7). Furthermore, it can thus be detected (by the detection device 7) whether the dispensing process is completed in the planned series.

Alternatively or in addition, as explained above, the dispensing device 3, property, or change in state of the dispensing device 3 and/or the substance 2 can be identified.

Figure 7:
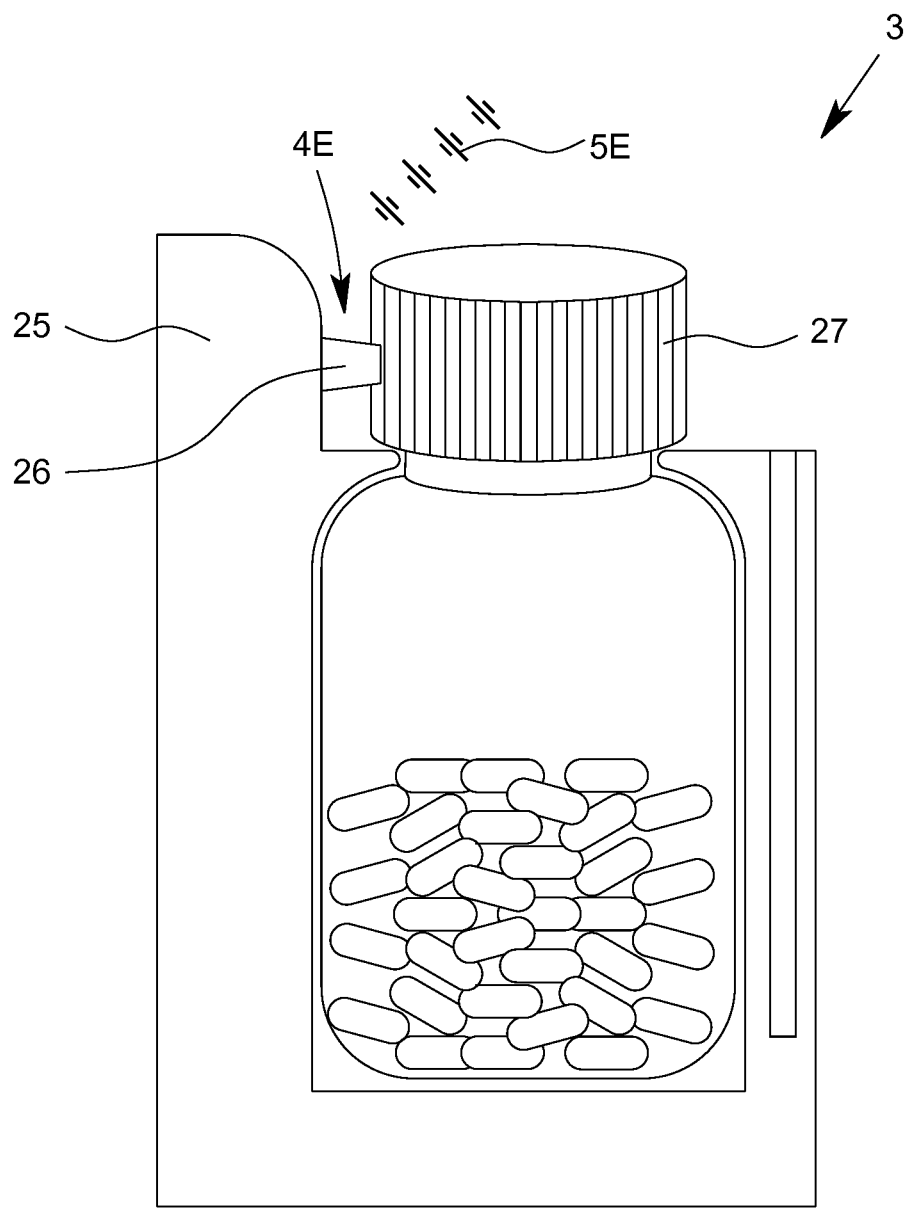
FIG. 7 shows another dispensing device according to the proposed solution

In another example, FIG. 7 shows a dispensing device 3 in the form of a cylinder with a sound generator 4E in the form of an accessory device 25, which in the illustrative example can be plugged into the dispensing device 3 or can be applied in a preferably reversible manner to the latter in some other way.

The sound generator 4 is formed here by a spring arm 26 in combination with a fluting of a closure 27 of the dispensing device 3. When opening the dispensing device 3, the spring arm generates a specific or characteristic clattering as a sound event 5E. The fluting can be designed for modulation of the sound event 5E.

However, beyond the depicted examples, various additional dispensing devices 3, sound generators 4A-4E, and/or sound events 5A-5E are possible.

In one aspect of this invention, a sound generator 4A-4E generates a sound event 5A-5D or is designed for this purpose, which corresponds to a manufacturer or is specific to a manufacturer. The corresponding sound event pattern 17A, 17B accordingly thus preferably has an assignment means, which identifies or assigns the manufacturer. In this way, a manufacturer identification of the dispensing device 3 or substance 2 can be made. Also, in any case, an affiliation of the dispensing device 3 or the substance 2 with a manufacturer can be detected. This information can be used in general to verify or to preclude detection of the dispensing system 3.

In one aspect of this invention, a sound generator 4A-4E generates a sound event 5A-5D or is designed for this purpose, which corresponds to an active ingredient concentration or is specific to an active ingredient concentration. Accordingly, a sound event pattern 17A, 17B that corresponds to the sound event 4A-4E preferably has an assignment means, which makes possible an identification or assignment of the active ingredient concentration. In this way, an active ingredient concentration of the substance 2 can be detected. On this basis, in particular together with the counting result, medication compliance can subsequently be determined.

In another aspect of this invention, the detection(s) or differentiation(s) of the dispensing device(s) 3 and/or the substance(s) 2 are counted or the detection device 7 is designed for this purpose. In particular, direct dispensing of the substance 2, dispensing processes or direct dispensing with a determined—or a type of—dispensing device(s) 3 are counted. The result of this is referred to as the counting result. In this case, this can be a count or amount or a size without reference or with a time reference, such as detections or differentiations or dispensing processes per time span or (average) time spans between dispensing processes.

In another aspect of this invention, the detection device 7 is designed to generate, to store one or more results 14 or information for medication compliance that is derived therefrom in a database and/or on an application device for automatic dispensing or for adapting an automatic dispensing of the substance 2, or to forward to other substances 2. This can, but does not have to, be done based on the counting or counting result.

In another aspect of this invention, the sound generator 4A-4E is an electroacoustic transducer, such as a piezo element, loudspeaker or the like, or has such a one. The electroacoustic transducer can be excited and/or activated in or causally by one step of the dispensing process in order to generate specific, as necessary also complex, sound events 5A-5E. In particular, it is possible with the electroacoustic transducer also to modulate complex data or data packets with reliability in the sound event 5A-5E.

In another aspect of this invention, the sound generator 4A-4E is a piezo element or other element for generating ultrasound, or it has such a one. A sound event 5A-5E in the ultrasound range makes possible or facilitates the detection based on the fundamental specificity of such sound events 5A-5E. Unlike sound events 5A-5E, ultrasound is generated less often by accident in the audible range and is contained at lower amplitude in ambient noise, thus facilitating detection.

In another aspect of this invention, the dispensing device 3 has as a sound generator 4A-4E a housing part that is preferably modifiable or designed specifically for the sound generation or amplification.

In another aspect of this invention, the sound generator 4 has one or more elastic elements such as pins, spring arms, elastic structures or spring-loaded structures. The latter are preferably designed by interaction with another part for generating the sound event 5A-5E. In particular, they interact with the surface structure 3D or counter-structure 3E in the dispensing process, forming the sound event 5A-5E. For example, one or more elastic elements is or are provided in or on a cap, or in general in or on a closure for a supply receptacle, in particular a medication reservoir.

In another aspect of this invention, a blister is provided as a sound generator 4A-4E. The latter, for example, can generate the sound event 5A-5E—for example corresponding to an active ingredient concentration or the like—by a modified blister film or a system that is coupled to the blister in the case of the removal of the content of a blister.

In another aspect of this invention, the sound event 5A-5E is used to identify a specific phase or a specific sequence of events in the dispensing process.

In other aspects of this invention, the detection device 7 is designed specifically to detect one or more of the described, specific sound events 5A-5E. To this end, the detection device 7 can use a corresponding specific sound event pattern 17A, 17B. Preferably based on the sound event pattern 17A, 17B, the detection device 7 automatically assigns corresponding information pertaining to the things to which the sound events 5A-5E are specific. Alternatively or in addition, the detection device 7 can have a microphone, which converts specific frequency ranges into electric currents or voltages, in particular audible frequencies and/or ultrasound.

In other aspects of this invention, the sound generator 4A-4E generates a continuous, preferably constant or single-frequency, sound wave. In this case, the sound event 5A-5E can consist in modifying this sound wave, in particular relative to frequency and/or amplitude.

In the following, a third embodiment of the dispensing device 3 according to the proposed solution will be discussed, in particular with reference to FIGS. 8 to 13. If not indicated otherwise or obvious from the context, all previous explanations with regard to the system 1 and the dispensing device 3 also apply to the third embodiment of the dispensing device 3.

The dispensing device preferably has a longitudinal or main axis A. Terms referring to an axis, such as "axial", "radial" or the like, preferably relate to the axis A. For example, an "axial" direction or movement is a direction or movement which is parallel to the axis A and a "radial" direction or movement is a direction or movement which is radial to the axis A.

The dispensing device 3 according to the third embodiment is preferably essentially configured identically to the dispensing device 3 according to the first embodiment which is shown in FIG. 2. The dispensing device 3 according to the third embodiment preferably only differs from the dispensing device 3 according to the first embodiment in the construction of the protecting element 3D.

The dispensing device 3 preferably has a main body 3H and a protecting element 3D.

The protecting element 3D preferably forms a lid and/or cover of the dispensing device 3, in particular for covering an axial end of the main body 3H. Particularly preferably, the protecting element 3D is or forms a cap.

The protecting element 3D is preferably detachable from and/or attachable to the main body 3H. Preferably, the protecting element 3D can be or is reversibly held on the main body 3H, in particular an axial end thereof, preferably by a latching and/or snapping mechanism.

The protecting element 3D can be covered by an additional cap or cover which is not shown in the Figures.

The protecting element 3D and/or dispensing device 7 is/are preferably designed for single use and/or is/are a disposable product.

The protecting element 3D preferably has or forms a sound generator 4A. The sound generator 4A of the dispensing device 3 according to the third embodiment is preferably similar to the sound generator 4A of the dispensing device 3 according to the first embodiment, wherein differences will be described hereinafter.

Preferably, all parts of the sound generator 4A are comprised by and/or integrated in the protecting element 3D. The protecting element 3D preferably completely comprises the sound generator 4A. The main body 3H does preferably not comprise the sound generator 4A or parts thereof.

The sound generator 4A is designed to generate, upon an actual or simulated preparation of a dispensing of the substance 2, at least one reproducible sound event 5A in an acoustic signal 6, the sound event 5A being specific to a property and/or change in state of the dispensing device 3.

The protecting element 3D is preferably configured to keep the substance 2 from being dispensed in an initial state of the dispensing device 3. The dispensing device 3 can preferably be transferred to an enabling state for enabling the dispensing of the substance 2, wherein the sound event 5A is generated upon transferring the dispensing device 3 to the enabling state.

Figure 8A:
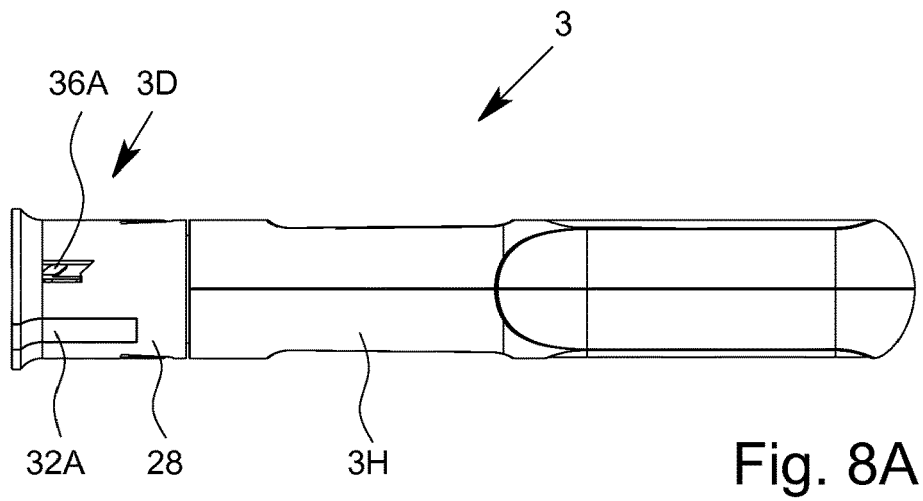
FIG. 8A shows a dispensing device according to a third embodiment in an initial state.
Figure 8B:
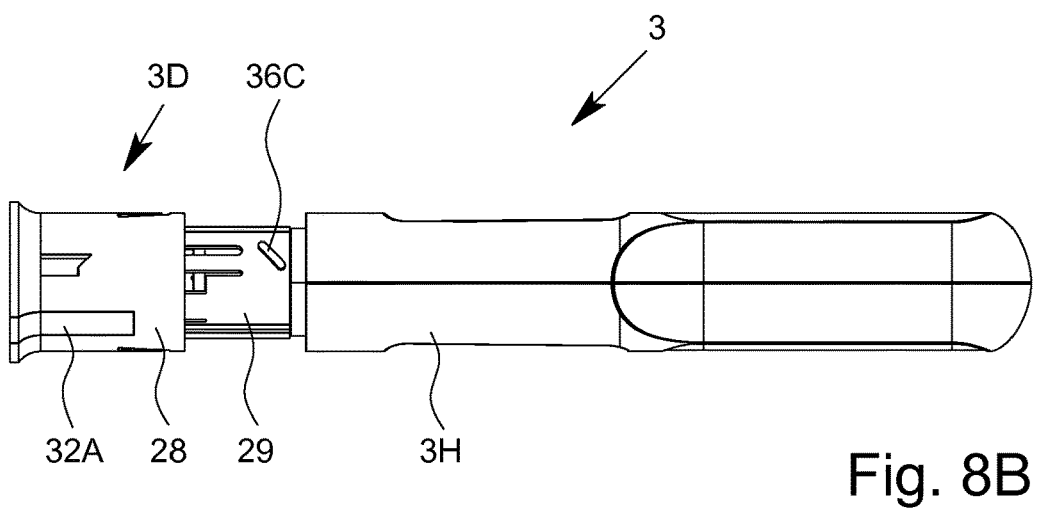
FIG. 8B shows the dispensing device according to the third embodiment in an intermediate state.
Figure 8C:
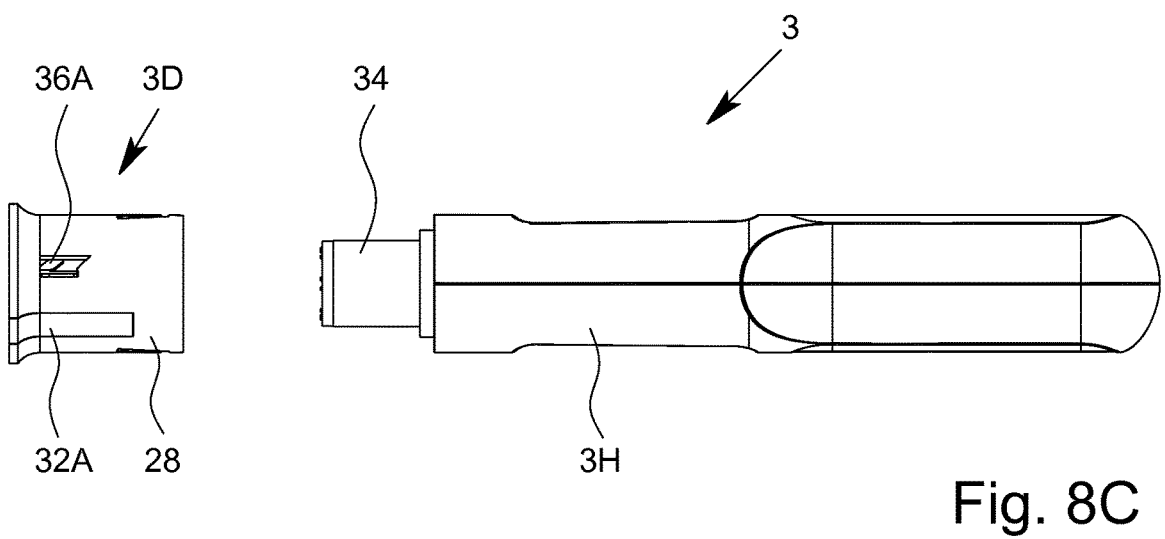
FIG. 8C shows the dispensing device according to the third embodiment in an enabling state.
Figure 9:
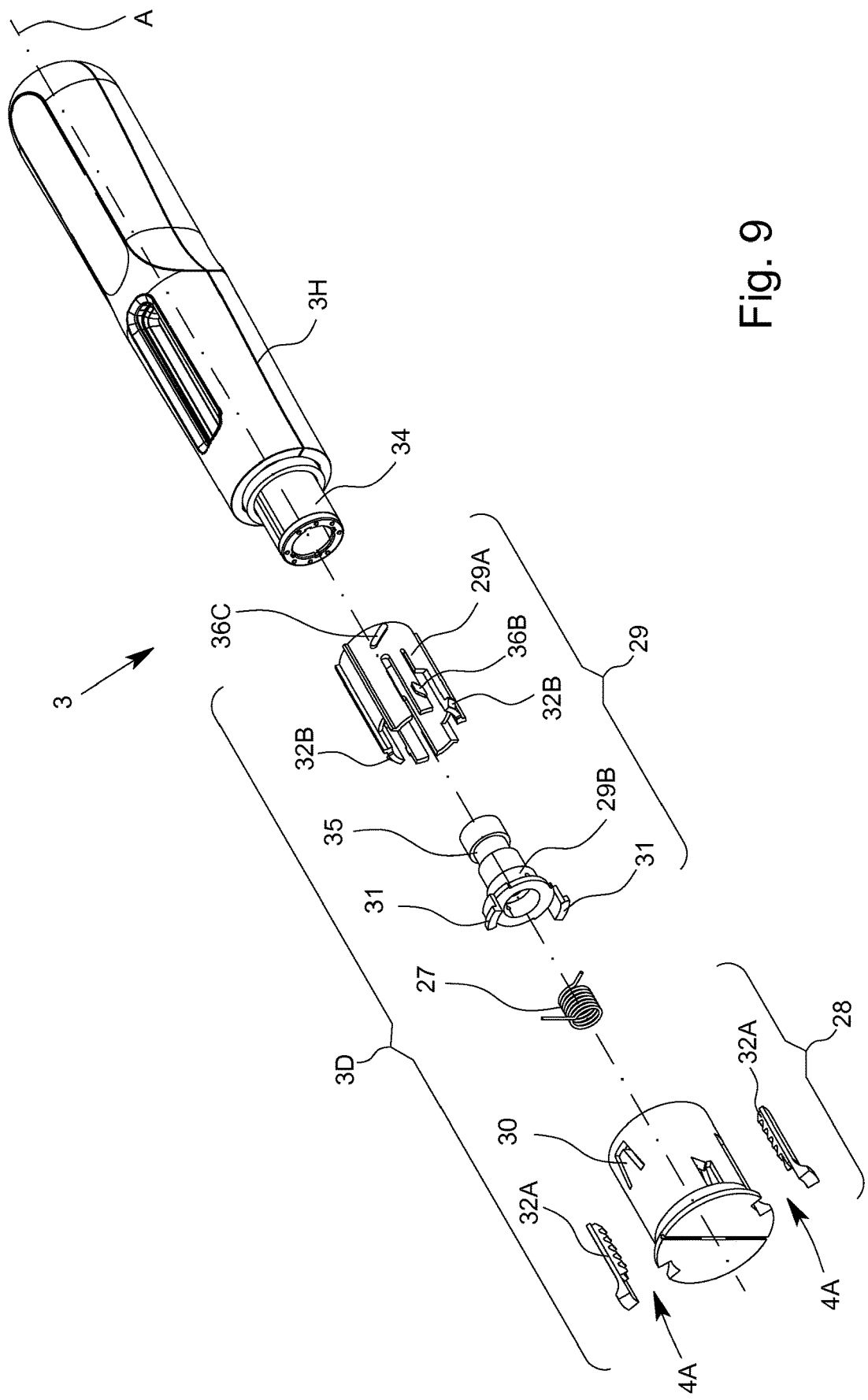
FIG. 9 shows an exploded view of the dispensing device according to the third embodiment.
Figure 10:
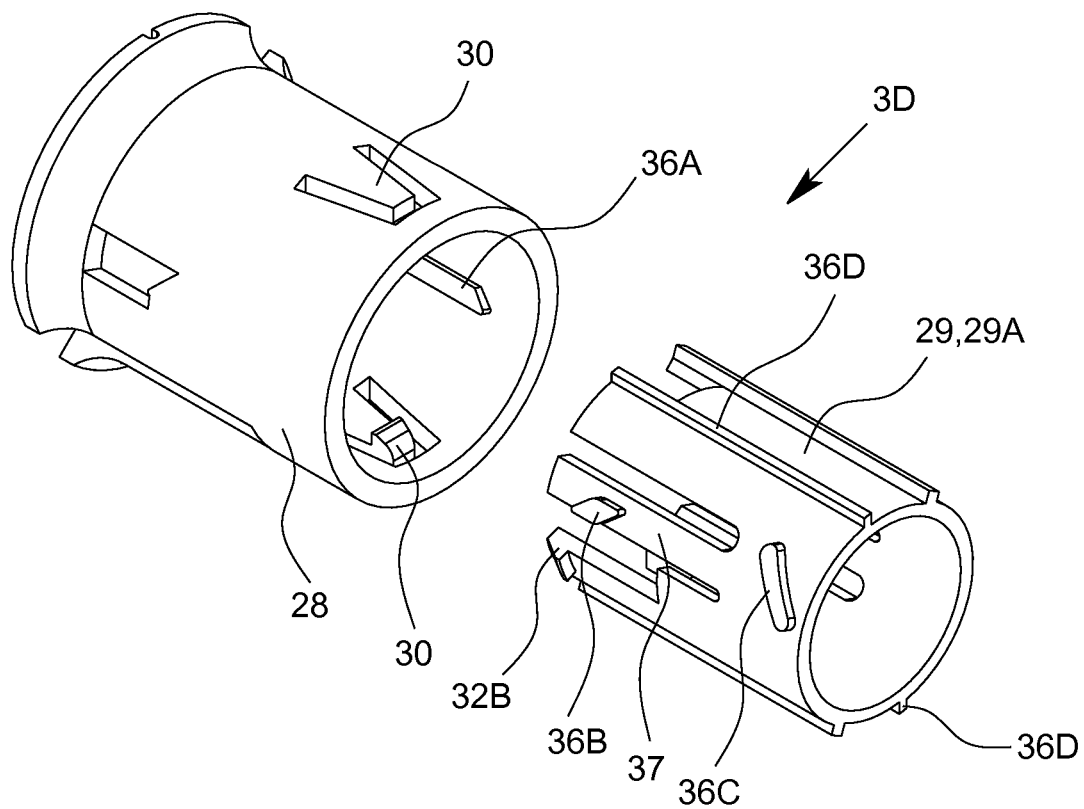
FIG. 10 shows an exploded view of a first part and a second part of the protecting element according to the proposed solution.

Different states of the dispensing device 3 are shown in FIG. 8. FIG. 8A depicts the initial state, FIG. 8C depicts the enabling state and FIG. 8B depicts an intermediate state which is adopted upon transferring the dispensing device 3 from the initial state to the enabling state.

The initial state is in particular the state in which the protecting element 3D, in particular the cap, is attached to the main body 3H of the dispensing device 3 and thus covers the main body 3H and/or prevents dispensing of the substance 2. The enabling state is in particular the state in which the protecting element 3D or cap has been removed from the main body 3H and thus dispensing of the substance 2 is enabled.

The protecting element 3D and/or the dispensing device 3 is/are preferably configured to generate the sound event 5A upon transferring the protecting element 3D and/or dispensing device 3 from the initial state to the enabling state. In particular, the protecting element 3D and/or dispensing device 3 is/are configured to generate the sound event 5A upon removing the protecting element 3D from the main body 3H.

The generated sound event 5A is preferably independent of the speed, force and/or other external parameters used for transferring the protecting element 3D or dispensing device 3 to the enabling state, in particular for removing the protecting element 3D from the main body 3H. In other words, the generated sound event 5A does not depend on the manner in which a user (not shown) removes the protecting element 3D or cap from the main body 3H, but the generated sound event 5A is always the same, regardless of for example whether the user removes the protecting element 3D slowly or quickly. This is in particular achieved by the construction of the protecting element 3D and/or an internal mechanism of the protecting element 3D having or forming the sound generator 4A and is conducive to the reproducible generation of the sound event 5A.

The protecting element 3D can preferably be positioned in different positions, as apparent from FIG. 8. In particular, the protecting element 3D has an activation position.

The protecting element 3D is preferably configured to automatically, immediately and/or necessarily generate the sound event 5A after reaching the activation position, particularly wherein the generated sound event 5A is independent of the manner in which the protecting element 3D is manipulated, for example whether the protecting element 3D is removed from the main body 3H slowly or quickly.

Preferably, the sound event 5A can only be generated if the protecting element 3D is being positioned in the activation position (before generation of the sound event 5A). In other words, positioning the protecting element 3D in the activation position is preferably a necessary condition without which the sound event 5A cannot be generated.

The activation position is preferably a position which has to be reached to enable generation of the sound event 5A. Preferably, the activation position is a defined position of the protecting element 3D which is defined or determined by the construction of the protecting element 3D.

A "manipulation" of the protecting element 3D and/or dispensing device 3 is preferably any action, in particular by a user, by which the position and/or state of the protecting element 3D and/or the dispensing device 3 are changed. In particular, manipulation of the protecting element 3D includes or means a process of removing the protecting element 3D from the main body 3H and/or moving different parts of the protecting element 3D relative to one another.

The protecting element 3D preferably has a drive element 27. The drive element 27 is preferably a spring, in particular a tension spring. Preferably, the drive element 27 is, in particular completely, arranged within the protecting element 3D or on the inside thereof.

The drive element 27 is preferably configured to be activated, in particular tensioned, by manipulating the protecting element 3D such that the activation position is reached, in particular by positioning or moving the protecting element 3D towards or in the actuation position.

Further, the drive element 27 is preferably configured to automatically, immediately and/or necessarily cause the generation of the sound event 5A after the protecting element 3D has reached the activation position.

The protecting element 3D preferably has a first part 28 and a second part 29. The first part 28 is preferably configured as a cap and the second part 29 is preferably configured as a sleeve which is in particular arranged or arrangeable within the cap, particularly coaxially with the cap. In particular, the first and second part 28, 29 are at least essentially cylindrical.

The first and second part 28, 29 are moveable relative to each other between an initial position and the activation position. The terms "initial position" and "activation position" denote different positions of the protecting element 3D and, thus, in particular different positions of the first and second part 28, 29 relative to each other.

Figure 11A:
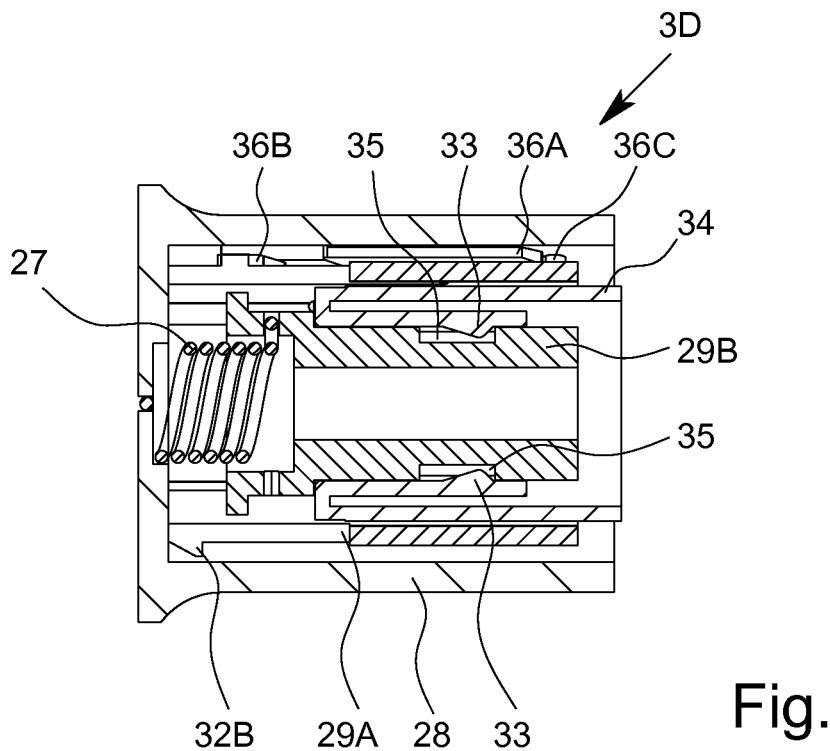
FIG. 11A shows a schematic section of the protecting element in an initial position.
Figure 11B:
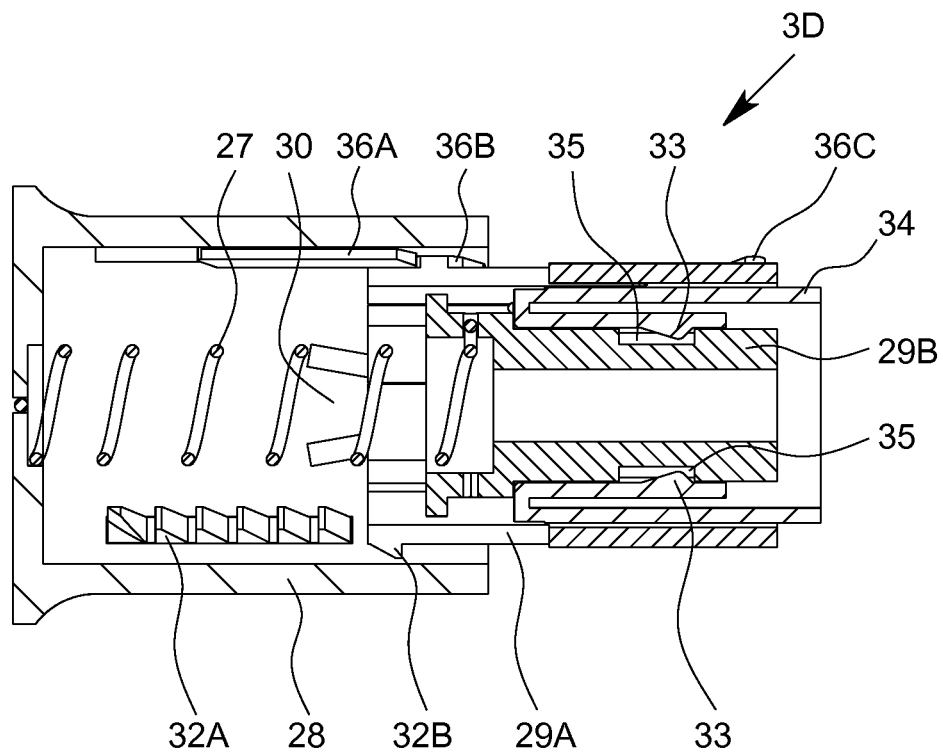
FIG. 11B shows a schematic section of the protecting element in an activation position.
Figure 12A:
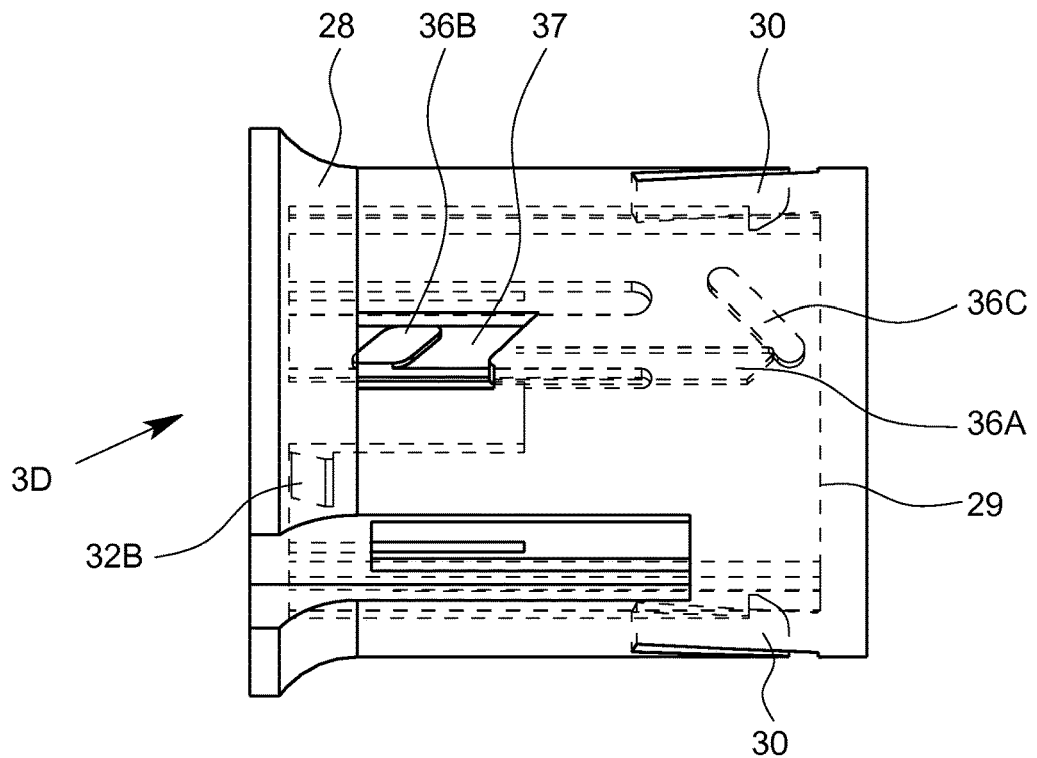
FIG. 12A shows a schematic view of the protecting element according to FIG. 11 in the initial position.
Figure 12B:
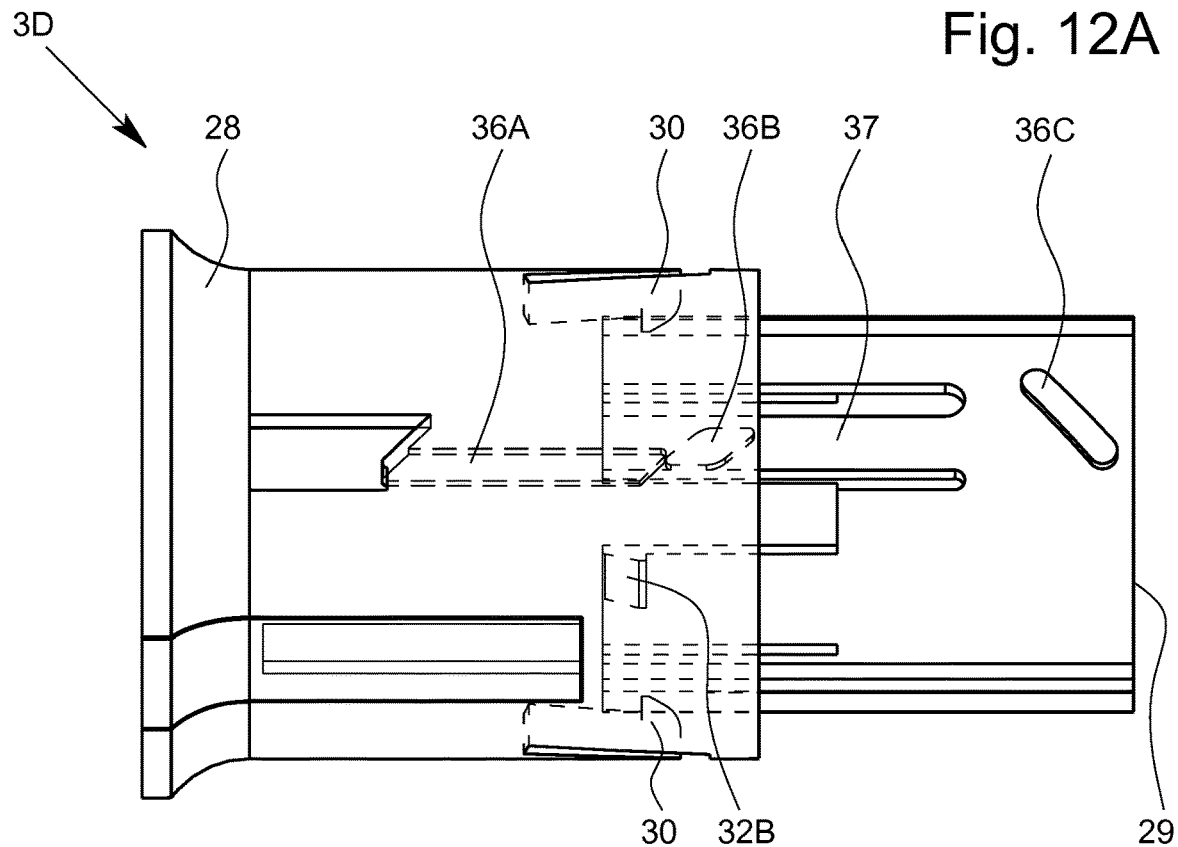
FIG. 12B shows a schematic view of the protecting element according to FIG. 11 in the activation position.

The initial position of the protecting element 3D is depicted in FIGS. 11A and 12A and the activation position is depicted in FIGS. 11B and 12B.

In the initial position, the second part 29 is preferably completely inserted into the first part 28. The initial position is preferably a resting position in which the protecting element 3D is held or pre-tensioned and/or into which the protecting element 3D returns when no external forces act on the protecting element 3D and/or drive the parts 28, 29 apart or prevent a moving of the parts 28, 29 relative to each other.

The activation position is in particular a position in which the first and second part 28, 29 have been moved relative to each other, in particular moved apart, with regard to the initial position. In the illustrative example, the activation position is a position in which the second part 29 has (partly) been moved out of the first part 28 and/or juts out of the first part 28.

The initial position and the activation position are preferably different axial and/or rotational positions of the first and second part 28, 29 relative to each other.

The activation position is preferably defined or determined by the construction or configuration of the first part 28 and the second part 29, as explained in more detail below.

It is noted that the "initial state" of the dispensing device 3 and the "initial position" of the protecting element 3D are not the same but are distinguished from each other. In FIG. 8A, the protecting element 3D is shown in the initial position in the dispensing device 3 is shown in the initial state. However, in FIG. 8B, the first and second part 28, 29 of the protecting element 3D have been moved relative to each other, so that the protecting element 3D is not in the initial position. In FIG. 8C, the protecting element 3D is again in the initial position (as described later), whereas the protecting element 3D has been completely removed from the main body 3H and, thus, the dispensing device 3 is in the enabling state.

The drive element 27 is configured to hold and/or pre-tension the protecting element 3D or first and second part 28, 29 in the initial position. The drive element 27 is preferably configured to be tensioned by moving the first and second sound part 28, 29 apart. Preferably, the drive element 27 is arranged and/or tensioned between the first part 28 and the second part 29. Further preferably, the drive element 27 is engaged with and/or attached to the first part 28 and/or the second part 29.

The first and second part 28, 29 are preferably linearly moveable relative to each other. As an alternative or addition, the first and second part 28, 29 are rotatable relative to each other, at least to a certain degree and/or in a certain range. In the illustrated example, the first and second part 28, 29 are both linearly moveable and—in a limited range—rotatable to each other, as explained in more detail below.

The second part 29 preferably has or is formed by several elements, in particular a sleeve element 29A and a fitting element 29B. In principle, the second part 29 could also be formed by only one piece. However, the two-piece construction with the sleeve element 29A and the fitting element 29B has proven advantageous for manufacturing and assembling the protecting element 3D or second part 29.

The sleeve element 29A is preferably configured as a sleeve and/or essentially cylindrical. The fitting element 29B is preferably inserted into and/or arranged coaxially with the sleeve element 29A. In particular, the sleeve element 29A has recesses which are configured for receiving or holding the fitting element 29B.

The sleeve element 29A and the fitting element 29B preferably form a unit, in particular wherein the sleeve element 29A and fitting element 29B are not movable and/or moved relative to another during use of the dispensing device 3 and/or protecting element 3D. In other words, the sleeve element 29A and fitting element 29B are preferably in a fixed position relative to each other. This can be achieved for example by fixedly attaching the sleeve element 29A and fitting element 29B to each other, for example by a latching mechanism and/or by providing a permanent connection between the sleeve element 29A and the fitting element 29B, for example by gluing, welding or the like.

The protecting element 3D preferably has a latching mechanism and/or stop for preventing the second part 29 from being detached or removed from the first part 28 and/or for preventing relative movement of the first and second part 28, 29 beyond the activation position.

The latching mechanism or stop preferably has or is formed by a pawl or an engagement hook 30, which is in particular arranged on the first part 28 and an engagement element 31 corresponding to and/or configured to engage with the engagement hook 30, preferably wherein the engagement element 31 is arranged on the second part 29, in particular the fitting element 29B.

The pawl or engagement hook 30 is preferably formed by a flexible arm which is in particular arranged and/or cut out from a cylindrical and/or peripheral wall of the first part 28. The engagement element 31 is preferably formed by a radially protruding element of the second part 29 or fitting element 29B, which is in particular arranged on an axial end of the second part 29 or fitting element 29B.

Particularly preferably, the latching mechanism or stop has or is formed by two engagement hooks 30 and two engagement elements 31 which are each arranged on radially opposing sides of the first part 28 or second part 29.

The latching mechanism or stop can be configured to reversibly hold the second part 29 or to irreversibly or inseparably connect the second part 29 to the first part 28, so that the second part 29 cannot be removed or detached from the first part 28 (without destroying the protecting element 3D, i.e. the first and/or second part 28, 29).

The sound generator 4A is preferably configured to generate the sound event 5A purely mechanically. In particular, the sound generator 4A and/or protecting element 3D comprises first and second sound generating elements 32A, 32B which are configured to (reproducibly) generate the sound event 5A.

In particular, the sound generator 4A is a ratchet and/or the sound event 5A is generated by the sound generating elements 32A, 32B by moving the sound generating elements 32A, 32B relative to each other. Preferably, the first sound generating element 32A comprises a rib surface structure or corrugated surface structure. The corresponding, second sound generating element 32B preferably has or is formed by a projection. By moving the projection over the rib structure or corrugated structure, a ratchet sound is generated.

Preferably, the first part 28 has or forms the first sound generating element 32A and the second part 29 has or forms the second sound generating element 32B. The first sound generating element 32A is preferably arranged on an inner wall of the first part 28 and the second sound generating element 32B is preferably arranged on an outer wall of the second part 29, in particular the sleeve element 29A.

The first sound generating element 32A is preferably attachable to the first part 28, detachable from the first part 28 and/or exchangeable. Preferably, the first sound generating element 32A is reversibly held or holdable on the first part 28, for example by a latching mechanism or the like. In this way, different protecting elements 3D and/or dispensing devices 3 can be provided with different sound generating elements 32A or different sound generators 4A, so that the sound generator 4A can be adapted to the substance 2 of the dispensing device 3 and so that the sound event 5A is specific for the substance 2.

Preferably, the sound generator 4A has or is formed by two identical pairs of corresponding sound generating elements 32A, 32B.

The protecting element 3D and/or sound generator 4A is preferably configured to generate the sound event 5A, preferably only and/or exclusively, after movement of the protecting element 3D from the initial position into the activation position and/or upon return of the protecting element 3D from the activation position to the initial position.

It is noted, that expressions as "return from the activation position to the initial position" or "movement from the activation position to the initial position" or the like do not necessarily mean that the protecting element 3D is actually again in the initial position at the end of the return or movement, respectively. In other words, the initial position does not need to be reached again but it is sufficient that the return or movement is essentially towards or in the direction of the initial position, in particular at least essentially opposite the movement from the initial position to the activation position, even without the protecting element 3D finally ending up in the initial position. Thus, movements starting from the activation positions which do not reach or end up in the initial position are preferably also included by expressions as "return from the activation position to the initial position" or "movement from the activation position to the initial position" or the like.

In the illustrative example, reaching the initial position at the end of the return from the activation position requires or includes a rotation back to the initial position, as explained in more detail below. In particular, this rotation, which preferably occurs after generation of the sound event 5A, can be omitted.

The protecting element 3D is depicted in the initial position in FIGS. 11A and 12A and in the activation position in FIGS. 11B and 12B.

The protecting element 3D or the parts 28, 29 is/are preferably movable or moved from the initial position to the activation position by, in particular axially, moving apart the first part 28 and the second part 29. Moving apart the first and second part 28, 29 preferably occurs automatically in a process of removing the protecting element 3D from the main body 3H, as in particular depicted in FIGS. 8A and 8B.

A "process of removing" the protecting element 3D is in particular a process by which or at the end of which the protecting element 3D is removed from the main body 3H. A process of removing the protecting element 3D preferably includes several positions of the protecting element 3D and/or states of the dispensing device 3. The actual removing of the protecting element 3D from the main body 3H preferably occurs only at the end and/or as a final step of the process, as will become clearer hereinafter.

The dispensing device 3 is preferably configured to move the protecting element 3D into the activation position upon a process of removing the protecting element 3D and/or the first part 28 from the main body 3H.

In particular, the dispensing device 3 or main body 3H, in particular a preferably at least essentially cylindrical needle protection 34 arranged within the main body 3H and/or (radially) surrounding the injection needle 3B, is configured to hold the second part 29 in a fixed position relative to the main body 3H upon a process of removing the protecting element 3D and/or the first part 28 from the main body 3H, while the protecting element 3D is moved from the initial position to the activation position by moving the first part 28 relative to the second part 29 and/or the main body 3H, in particular moving the first part 28 away from the main body 3H.

The process of removing the protecting element 3D from the main body 3H thus preferably involves a step in which the first part 28 is already moved away from the main body 3H while the second part 29 has not yet moved relative to the main body 3H. This is in particular shown in FIG. 8B.

The dispensing device 3 preferably has a detent 33 for engaging with the protecting element 3D, in particular the second part 29, particularly preferably the fitting element 29B. The detent 33 is preferably configured for holding, at least temporarily, the second part 29 in a fixed position relative to the main body 3H upon the process of removing the protecting element 3D from the main body 3H.

The detent 33 is preferably arranged on a flexible arm which is in particular arranged on an inner wall of the main body 3H, in particular the needle protection 34.

The second part 29, in particular the fitting element 29B, preferably has an undercut 35 for engagement with the detent 33. The undercut 35 is preferably configured as a notch which in particular circumferentially runs around the second part 29 or fitting element 29B The detent 33 and/or flexible arm is preferably configured to release the second part 29 from the detent 33 when the protecting element 3D and/or first part 28 has reached the activation position and the protecting element 3D and/or first part 28 is (subsequently) further moved away from the main body 3H. The force by which the second part 29 is held by the stop or engagement hook 30 is preferably larger than the force by which the second part 29 is held with the detent 33, so that the engagement between the detent 33 and the second part 29 is released when the protecting element 3D is already in the activation position and then further moved away from the main body 3H.

Preferably, the drive element 27 is configured to be activated, in particular tensioned, upon movement of the protecting element 3D or the parts 28, 29 from the initial position to the activation position.

The protecting element 3D is preferably configured to return into the initial position when or after the protecting element 3D has been moved from the initial position into the activation position. However, a return into the initial position is not necessary, as explained above. Preferably, the sound event 5A is generated after the activation position has been reached and/or during moving or return of the protecting element 3D or parts 28, 29, especially to the initial position.

The movement from the activation position to the initial position preferably takes place automatically and/or immediately after the activation position has been reached. In particular, the drive element 27 is configured to drive the return of the protecting element 3D from the activation position to the initial position. As explained before, the drive element 27 is preferably activated or tensioned by moving from the initial position into the activation position, so that the return from the activation position to the initial position is caused or driven by the elastic restoring force of the tensioned spring or drive element 27. In other words, the movement from the activation position to the initial position preferably takes place purely mechanically.

The protecting element 3D is preferably configured so that no sound or sound event 5A is generated upon movement of the protecting element 3D from the initial position to the activation position and/or that the sound event 5A is (only) generated after movement from the initial position the activation position, in particular upon movement of the protecting element 3D from the activation position to the initial position. In other words, the protecting element 3D and/or sound generator 4A is preferably configured so that the sound generating elements 32A, 32B do not interact or contact each other upon movement from the initial position into the activation position and/or that the sound generating elements 32A, 32B (only) interact or contact each other after movement from the initial position the activation position, in particular upon movement from the activation position to the initial position so that the sound event 5A is generated.

The non-interaction of the sound generating elements 32A, 32B upon movement from the initial position towards the activation position is also conducive to an easy operation of the dispensing device, in particular for a smooth removal of the protecting element 3D from the main body 3H. Namely, upon removal of the protecting element 3D from the main body 3H, a considerable force is already needed for working against the spring tension of the drive element 27, which force would be further increased through interaction of the sound generating elements 32A, 32B upon movement from the initial position towards the activation position. Thus, the non-interaction of the sound generating elements 32A, 32B is advantageous for an easy operation, in particular for keeping the force needed for removal of the protecting element 3D at an acceptable level.

The protecting element 3D preferably has a guiding which is configured so that upon movement of the protecting element 3D from the initial position into the activation position, the sound generating elements 32A, 32B do not interact, and so that upon movement of the protecting element 3D from the activation position to the initial position, the sound generating elements 32A, 32B interact and generate the sound event 5A.

The guiding is preferably configured to rotate the second part 29 when and/or (immediately) after the activation position is reached. Thus, upon movement from the initial position to the activation position, the second part 29 is preferably arranged in a different rotational position relative to the first part 28 than upon movement from the activation position back to the initial position. By the rotation, it is in particular achieved that the sound generating elements 32A, 32B do not interact or contact each other upon movement from the initial position to the activation position and/or that the sound generating elements 32A, 32B (only) interact or contact each other and thus generate the sound event 5A upon movement from the activation position to the initial position.

The guiding is preferably configured to ensure that the sound event 5A is only generated after the activation position has been reached.

The guiding preferably has or is formed by several guiding elements, in particular a first guiding element 36A, a second guiding element 36B, a third guiding element 36C and/or a fourth guiding element 36D.

The first, second, third and/or fourth guiding element(s) 36A-36D is/are preferably (each) configured as a jut or protrusion.

Preferably, the protecting element 3D comprises two identical guidings which are arranged on radially opposing sides of the protecting element 3D.

The first part 28 preferably has the first guiding element 36A. The first guiding element 36A is preferably arranged on and/or projects from an inner, in particular cylindrical, wall of the first part 28, as in particular shown in FIG. 10. Preferably, the first guiding element 36A extends axially and/or is elongated.

The first guiding element 36A is preferably at least essentially in the form of quadrilateral, wherein two sides of the guiding element 36A run parallel to the axis A and the other two sides are slanted with respect to the axis A. Particularly preferably, the first guiding element 36A is at least essentially in the form a parallelogram.

The second part 29 preferably has the second, third, fourth and/or fifth guiding element 36B to 36I. The second, third and/or fourth guiding element(s) 36B-36D is/are preferably arranged on and/or project(s) from an outer, in particular cylindrical, wall of the second part 29, as in particularly shown in FIG. 10.

The second guiding element 36B is preferably configured to contact the first guiding element 36A and/or to slide along the first guiding element 36A.

The second guiding element 36B is preferably at least essentially in the form of a quadrilateral. The second guiding element 36B preferably has two slides running parallel to the axis A and two slides which are slanted with respect to the axis L. Particularly preferably, the first guiding element 36 is in the form of a parallelogram or rhombus.

The second guiding element 36B is preferably configured to run around the first guiding element 36A upon moving the protecting element 3D from the initial position to the activation position and back to the initial position.

The second guiding element 36B is preferably arranged at a free end of a flexible arm 37 of the second part 29. The arm 37 is preferably configured to be at least essentially circumferentially deflected upon movement of the protection element 3D from the initial position into the activation position and/or to flip back before and/or upon movement of the protecting element 3D from the activation position to the initial position.

The arm 37 is preferably formed in one piece with the second part 29, in particular the sleeve element 29A. In particular, the arm 37 is formed by axial cutouts of the cylindrical wall of the sleeve element 29A.

The fourth guiding element 36D is preferably configured as axially running rail. The fourth guiding element 36D is preferably configured to limit a rotation of the second part 29 relative to the first part 28, in particular by contacting the engagement hook 30.

The functionality of the guiding is explained in the following in particular with reference to FIGS. 11 to 13.

In FIGS. 11A and 12A, the protecting element 3D is shown in the initial position. In FIGS. 11B and 12B, the protecting element 3D is shown in the activation position. FIG. 13 shows a bottom view of the protecting element 3D in the initial position.

Figure 13:
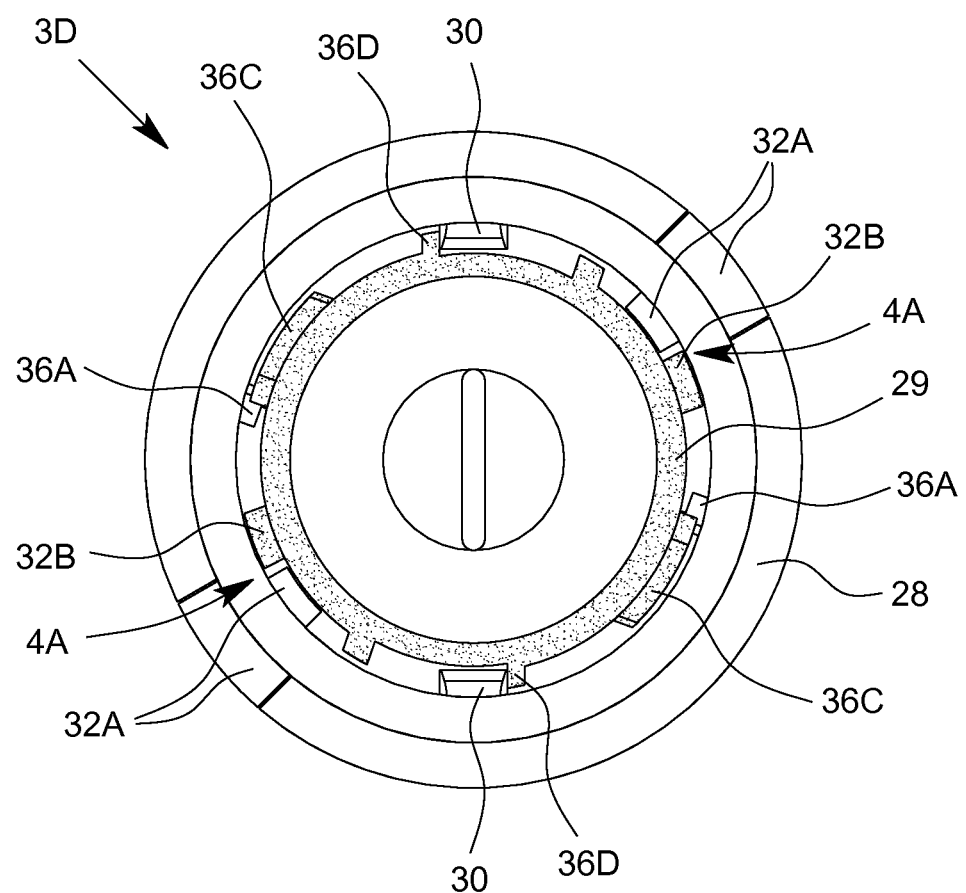
FIG. 13 shows a bottom view of the protecting element according to FIG. 11.

In the initial position, the sound generating elements 32A, 32B are offset from each other in the circumferential direction, as in particular visible in FIG. 13. Further, the engagement hook 30 contacts the fourth guiding element 36D, preferably so that a rotation of the second part 29 in clockwise direction in FIG. 13 is prevented.

As can be seen in FIGS. 12A and 13A, the first and second guiding elements 36A, 36B overlap in axial direction, so that the slanted sides of the first and second guiding elements 36A, 36B come into contact when the protecting element 3D is moved from the initial position towards the activation position.

As a rotation of the second part 29 in clockwise direction in FIG. 13 is prevented by the engagement hook 30 and the guiding elements 36A 36B overlap in axial direction, the flexible arm 37 with the second guiding element 36B is forced to bend or deflect, in particular in circumferential direction, upon further movement of the protecting element 3D towards the activation position when the guiding elements 36A, 36B come into contact.

The deflection of the arm 37 preferably builds up a restoring force in the arm 37 and/or presses the second guide element 36B, in particular an axial side thereof, against the first guide element 36A, in particular an axial side thereof.

Upon further moving the first and second parts 28, 29 apart, the activation position is reached. The activation position is in particular the position in which the second guide element 36B has reached the axial end of the first guide element 36A, as shown in particular in FIG. 12B. In particular, the activation position is a reversal point of the protecting element 3D and/or the position in which the second part 29 is caused to rotate and/or to move or slide back to the initial position in a different rotational position and/or along a different path and/or on a different axial side of the first guide element 36A than on the way from the initial position to the activation position.

In the activation position, the engagement hook 30 preferably engages the engaging element 31.

When or immediately after the activation position is reached, the restoring force of the bent or deflected arm 37 preferably causes the arm 37 to move or flip back into its rest position, i.e. the position in which the arm 37 is in the initial position of the protecting element 3D. By this, the second guide element 36B is moved relative to the first guide element 36A, in particular so that the second guide element 36B passes the corner at the end of the first guide element 36A and/or slanted edges of the guide elements 36A, 36B contact each other.

The spring or drive element 27 is preferably tensioned upon movement of the protection element 3D from the initial position to the activation position, as shown in FIGS. 11A and 11B.

Thus, the drive element 27 preferably causes or drives a movement of the second part 29 back towards the initial position when or immediately after the activation position has been reached or passed.

Upon return from the activation position to the initial position, the second guide element 36B preferably slides along the first guide element 36A, in particular on the axial side opposite to the axial side along which the second guide element 36B has slid upon movement from the initial position to activation position.

The movement of the second guide element 36B along the first guide element 36A upon movement from the activation position to the initial position preferably involves a rotation of the second part 29 relative to the first part 28, in particular in the anti-clockwise direction in FIG. 13. This is in particular effected by the slanted edge of the first guide element 36A and the circumferential movement of the second guide element 36B which is caused thereby. By this rotation, the rotational position of the first and second part 28, 29 relative to each other is changed in such a way that the sound generating elements 32A, 32B of the sound generator 4A interact and generate the sound event 5A upon movement from the activation position the initial position.

The third guide element 36C is preferably slanted with respect to the axis A and/or the first guide element 36A, so that towards the end of the movement from the activation position to the initial position, a rotation of the second part 29 back into the initial position is effected by the interaction between the first guide element 36A and the third guide element 36C.

To summarize, removing the protecting element 3D from the main body 3H and/or generating the sound event 5A preferably goes as follows:

In the beginning, the protecting element 3D, in particular in the form of a cap, is attached to the main body 3H. In this position, the protecting element 3D is an initial position and the detent 33 engages the second part 29.

For removing the protecting element 3D from the main body 3H, a user (not shown) pulls the first part 28 away from the main body 3H, in particular in axial direction. By this, the first and second part 28, 29 are moved relative to each other, while the second part 29 is held by the detent 33 and, thus, it does not move relative to the main body 3H. By the relative movement of the first and second part 28, 29, the drive element 27 is preferably tensioned.

Upon this movement, the second guide element 36B preferably slides along the first guide element 36A, in particular wherein the flexible arm 37 deflects, in particular circumferentially or upwards in FIGS. 11 and 12.

The user preferably moves the first part 28 away from the main body 3H until the activation position is reached.

When the activation position is reached or passed, the arm 37 preferably flips back so that the second guide element 36B is moved around the first guide element 36A and/or on the opposite side of the guide element 36A, in FIG. 12 the lower side of the guide element 36A.

Further, the second part 29 is released from the detent 33 when or shortly after the activation position is reached. This leads to a quick movement of the protecting element 3D towards the initial position, in particular driven by the drive element 27.

Further, the second part 29 has been rotated in the anti-clockwise direction in FIG. 13 upon reaching or passing the activation position, in particular by the arm 37 flipping back. By this rotation, the second part 29 is brought into a rotation position relative to the first part 28 that makes possible an interaction of the sound generating elements 32A, 32B.

By the quick movement from the activation position to the initial position, the sound event 5A is generated by the sound generating elements 32A, 32B that slide along each other.

Towards the end of the movement back to the initial position, the third guide element 36C preferably contacts the first guide element 36A and thereby causes a rotation (in particular clockwise in FIG. 13) of the second part 29 back into the initial position. This is, however, not mandatory.

The protecting element 3D, in particular the guiding, can also have a securing device for preventing a contact and/or interaction between the sound generating elements 32A, 32B upon movement from the initial position to the activation position, for example a respective guiding element, a stop, a latching element or the like. In particular, this securing device is configured to prevent a rotation (in particular in anti-clockwise direction in FIG. 13) of the second part 29 relative to the first part 28 upon movement from the initial position to the activation position. The securing element is preferably provided to ensure that the second guide element 36B slides along the correct side of the first guide element 36A, as described above, upon movement from the initial position to the activation position. In this way, incorrect operation by a user can be prevented. In particular, it can be prevented that the parts 28, 29 are rotated relative to each other when the protecting element 3D is removed from the main body 3H, which could potentially happen when the protecting element 3D is slightly twisted at the beginning of the movement from the initial position to the activation position.

The securing device is preferably arranged on the first and/or second part 28, 29. Preferably, the securing device is configured to contact, at least in the initial position and/or upon movement from the initial position to the activation position, one of the guiding elements 36A-36D, in particular the first guiding element 36A or the fourth guiding element 36D.

The protecting element 3D preferably has a damping device for controlling, damping and/or reducing the speed and/or acceleration of the movement of the protecting element 3D from the activation position to the initial position.

The damping device can for example be realized by a reinforcement of parts of the protecting element 3D, in particular the sound generating elements 32A, 32B, so that the pressure by which the sound generating elements 32A, 32B, are pressed against each other as increased.

Other possible solutions are a cylinder-piston arrangement realizing a damping and/or a regulation of air escaping from the protecting element 3D in order to realize a pneumatic break which damps the movement from the activation position to the initial position.

As an alternative or in addition, it is also conceivable to change the exact design of this sound generating elements and/or the spring forces, for example of the drive element 27 and/or the flexible arm 37, and/or to provide an additional spring or tensioning device.

Figure 14:
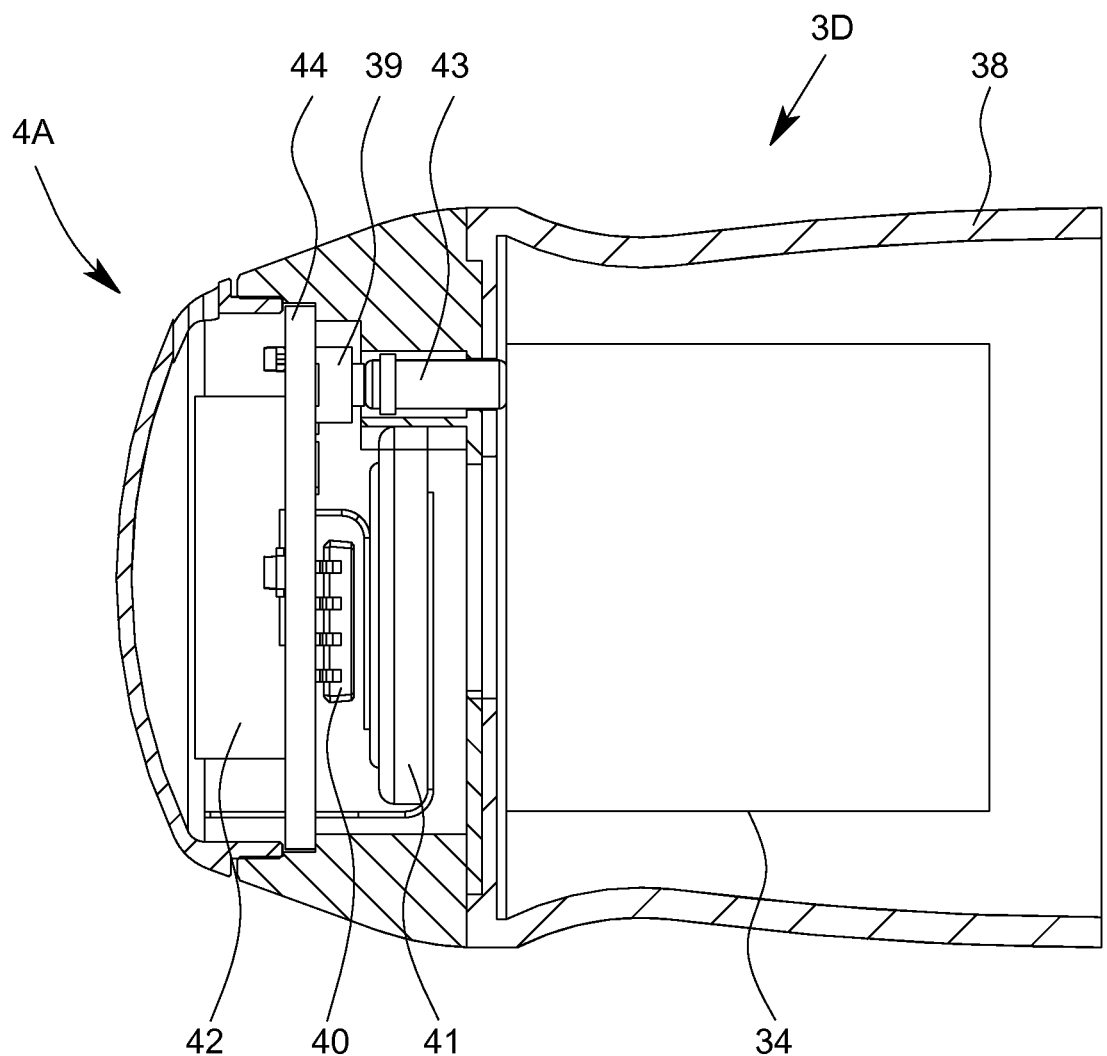
FIG. 14 schematically shows a further embodiment of a protecting element according to the proposed solution.

A further embodiment of the protecting element 3D and/or sound generator 4A is shown in FIG. 14.

Whereas the sound generator 4A of the protecting element 3D according to FIGS. 8 to 13 preferably works purely mechanically, the sound generator 4A of the embodiment shown in FIG. 14 preferably works electronically.

The explanations with regard to the protecting element 3 according to the embodiment shown in FIGS. 8 to 13 preferably also apply to the protecting element according to the embodiment shown in FIG. 14, unless indicated otherwise or obvious from the context.

In particular, the protecting element 3D forms a lid and/or cover of the dispensing device 3, in particular in the form of a cap. Further, the protecting element 3D preferably has or forms the sound generator 4A.

The protecting element 3D preferably has a housing 38, in particular in the form of a cap, preferably wherein in the sound generator 4A is arranged inside the housing 38 or integrated into the housing 38. The housing 38 can have or be formed by several parts.

The protecting element 3D and/or sound generator 4A preferably has a switch 39, an electronic module or electronics 40, a battery 41, and/or an electroacoustic transducer 42.

The sound generator 4A and/or electroacoustic transducer 42 is preferably configured to generate the sound event 5A. The battery 41 is preferably configured to supply the electronics 40 and/or transducer 42 with (electrical) energy.

The switch 39 is preferably configured to be actuated upon removing the protecting element 3D from the main body 3H, in particular the needle protection 34. Preferably, the switch 39 is a biased switch.

Preferably, the protecting element 3D has a, preferably spring-loaded, pin 43 arranged between the main body 3H or needle protection 34 and the switch 39. When the protecting element 3D is attached to the main body 3H of the dispensing device 3, the pin 43 preferably contacts the switch 39 and/or the needle protection 34 or another part of the main body 3H. However, other solutions are also possible here. In particular, the pin 43 can be omitted.

It is in particular possible that the switch 39 or an actuation element thereof is configured to be pressed down by the main body 3H and/or pin 43 when the protecting element 3D is attached to the main body 3H and/or that the switch 39 is actuated by moving apart the main body 3H and protecting element 3D.

The switch 39 is preferably functionally coupled with the electronic module or electronics 40. The electronics 40 are preferably configured to control the electroacoustic transducer 42 such that the sound event 5A is generated upon actuation of the switch 39.

The electronics 40 preferably have or form a control and/or processor for controlling the electroacoustic transducer 42.

The switch 39, electronics 40, battery 41 and/or electroacoustic transducer 42 are preferably arranged and/or mounted on and/or coupled via a printed circuit board 44. The electroacoustic transducer 42 is preferably arranged on a side of the printed circuit board 44 which is opposite the main body 3H when the protecting element 3D is attached to the main body 3H.

The electroacoustic transducer 42 preferably has or is formed by a piezo transducer or piezoelectric transducer.

The transducer 42 is preferably configured to generate a sound event 5A having a frequency of more than 2 kHz and/or less than 40 kHz, in particular a frequency of about 4 kHz and/or harmonics or whole multiples thereof, for example 8 kHz, 12 kHz, 16 kHz and/or 20 KHz. It is particularly preferred that the sound event 5A has only frequencies in the ultrasonic range and/or frequencies of more than 16 kHz. Particularly preferably, the sound event has a frequency of about 20 kHz. This has proven advantageous because on the one side, these frequencies cannot be detected by humans and thus do not constitute acoustic harassments of humans. On the other hand, it is preferably easier to detect an ultrasonic sound event 5A in the acoustic signal 6 because there are less background noises in the ultrasonic range.

The electronics 40 can also be configured for generating multiple and/or different sound events 5A with the transducer 42. Different sound events can differ for example in length, frequency, speed, loudness, spectral range, sequence of tones and/or frequencies or the like. In this way, the protecting element 3D and/or sound generator 4A and/or sound event 5A can be adapted to or made specific for different dispensing devices 3, in particular the substance 2 which is to be dispensed with the dispensing device 3.

The various aspects of this invention that are explained in the general part, in the embodiments, and in the claims can in each case be implemented individually as well as in combination and can be advantageous, even when not every possible advantageous combination is explained separately.

Additional aspects of this invention are:

1. System for monitoring an actual or simulated preparation, performing, and/or post-processing of a dispensing—referred to below as dispensing process—of an administrable, preferably pharmaceutical, substance, having:

a dispensing device for dispensing the substance, wherein the dispensing device has at least one sound generator, which is designed to generate in the dispensing process at least one sound event in an acoustic signal, in an acoustic signal, the sound event being specific to a property or change in state of the dispensing device, and a detection device for checking the acoustic signal for the at least one sound event in order to make possible a detection of the property or change in state of the dispensing device.

2. System according to Aspect 1, characterized in that the sound generator(s) is/are designed so that the sound event or the sound events in the dispensing process is or are generated necessarily and in a reproducible manner.

3. System according to one of the preceding aspects, characterized in that the sound generator is a structure that is not required for the dispensing process and/or is specifically designed for the generation of the sound event.

4. System according to one of the preceding aspects, characterized in that the sound generator is or has a ratchet, flapper, vibrating bell, rattle, whistle or structure for generating a reproducible plopping, clacking, clicking, screeching, clattering, grinding, rattling, hissing, squeaking, buzzing, whistling or is or has oscillations caused in particular by a stick-slip effect.

5. System according to one of the preceding aspects, characterized in that a protecting element of the dispensing device has or forms the sound generator, wherein the protecting element keeps the substance from being dispensed in an initial state and with generation of the sound event can be transferred into an enabling state for enabling the dispensing of the substance.

6. System according to one of the preceding aspects, characterized in that the sound generator is set up for generating in the acoustic signal a sequence of more than two sound events that are separated from one another and that follow one another in time in the course of the dispensing process.

7. System according to one of the preceding aspects, characterized in that the dispensing device has at least two different sound generators, which are designed so that in different phases of the dispensing process, which phases follow one another in time, a first sound event and a second sound event-preferably different from the first—are generated.

8. System according to one of the preceding aspects, characterized in that the detection device for detecting the property or change in state of the dispensing device by checking the acoustic signal is designed for the at least one sound event.

9. System according to Aspect 8, characterized in that the detection device is designed to compare the acoustic signal to one or more sound event pattern(s) and in this way to detect the at least one sound event in the acoustic signal, wherein sound event patterns are previously known information that corresponds to the sound events, that is similar to the sound events, or is derived therefrom.

10. System according to Aspect 9, characterized in that the detection device has a correlation module for generating a correlation of the acoustic signal with one or more sound event patterns.

11. System according to one of Aspects 8 to 10, characterized in that the detection device is designed to determine the property or change in state of the dispensing device when at least one sound event is detected in the acoustic signal based on the detected sound event.

12. System according to one of the preceding aspects, characterized in that the detection device is designed to distinguish between different sound events of the same, similar, or different dispensing devices.

13. System according to one of the preceding aspects, characterized in that the detection device has an output device for outputting a result of the checking of the acoustic signal, preferably wherein the detection device is designed for signaling with the output device the detection or for outputting the property or change in state of the dispensing device or a characteristic value of said change.

14. System according to one of the preceding aspects, characterized in that the detection device has or forms an analysis device for examining multiple sound events, detected in the check, for a predetermined sequence or order.

15. System according to one of the preceding aspects, characterized in that the detection device is designed to output a result, when it detects that the acoustic signal has a sequence of sound events that follow one another in time and that correspond to the course of steps of the dispensing process, or to output an error, when it detects that the acoustic signal does not have any sequence of sound events that follow one another in time and that correspond to the course of steps of the dispensing process.

16. System according to one of the preceding aspects, characterized in that the system has multiple dispensing devices, which are distinguished relative to the substance and the sound generator and are otherwise designed identically or similarly, so that the identical sound event or acoustic signal can be generated by the identical or similar dispensing devices with the same properties relative to the substance, and different sound events or acoustic signals can be generated by the identical or similar dispensing devices with different properties relative to the substance.

17. System according to one of the preceding aspects, characterized in that a part of the dispensing device—preferably a packaging, a primary packaging, a secondary packaging, a cap, a shell, a protective system, a mechanism, a stop, a pressure generator, an unlocking system, a triggering system, a flow path, and/or a dispensing device for ejecting the substance—has or forms the sound generator.

18. Detection device for checking an acoustic signal for a sound event that is generated by a sound generator of a dispensing device of a system according to one of the preceding aspects and is specific to a property or change in state of the dispensing device, sound event for detection of a dispensing process, carried out with the dispensing device, of the administrable, preferably pharmaceutical, substance.

19. Method for monitoring an actual or simulated preparation, performing, and/or post-processing of a dispensing-referred to as dispensing process below—of an administrable, preferably pharmaceutical, substance, wherein an acoustic signal is examined for a sound event that is specific to a property or change in state of the dispensing device, which sound event can be generated in the case of the dispensing process.

20. Use of a mobile terminal device, preferably a Smartphone, a tablet computer, and/or wearable devices, in particular a Smartwatch or a fitness arm band, for checking an acoustic signal for at least one sound event that is specific to a property or change in state of a dispensing device, which sound event can be generated in the case of an actual or simulated preparation, performing, and/or post-processing of a dispensing-referred to as dispensing process below—of an administrable, preferably pharmaceutical, substance, with a sound generator of the dispensing system, in order to make possible a detection of a property or change in state of the dispensing device.

21. Computer program product that has program code means, which, when they are implemented, perform a method according to Aspect 19, in particular a computer-readable—preferably non-volatile-storage medium that has instructions, which, when they are implemented on a processor, implement the method according to Aspect 19.

REFERENCE SYMBOL LIST

1 System
2 Substance
3 Dispensing device
3A Carpule
3B Injection needle
3C Actuator
3D Protecting element
3E Surface structures
3F Counter-structures
3G System
3H main body
4A Sound generator
4B Sound generator
4C Sound generator
4D Sound generator
4E Sound generator
5A Sound event
5B Sound event
5C Sound event
5D Sound event
5E Sound event
6 Signal
7 Detection device
8 Microphone
9 Processor
10 Output device
11 Interface
12 Data link
13 Database
14 Result
15 Analysis device
16 Correlation module
17A First sound event pattern
17B Second sound event pattern
18 Secondary packaging
19 Tear flap
20 Predetermined scoring line
21 Primary packaging
22 Receptacle
23 Film
24 Adhesive
25 Accessory device
26 Spring arm
27 Drive element
28 First part
29 Second part
29A Sleeve element
29B Fitting element
30 Engagement hook
31 Engagement element
32A First sound generating element
32B Second sound generating element
33 Detent
34 Needle protection
35 Undercut
36A First guiding element
36B Second guiding element
36C Third guiding element
36D Fourth guiding element
37 Arm
38 Housing
39 Switch
40 Electronics
41 Battery
42 Electroacoustic transducer
43 Pin
44 Printed circuit board
A Axis
t1 Time span
t2 Time span
t3 Time span
t4 Time span
t5 Time span

What is claimed is:

1. System for monitoring an actual or simulated preparation, performing, and/or post-processing of a dispensing- referred to below as dispensing process—of an administrable, substance, having:
a dispensing device for dispensing the substance, wherein the dispensing device has at least one sound generator, which is designed to generate in the dispensing process at least one sound event in an acoustic signal, the sound event being specific to a property or change in state of the dispensing device, and
a detection device for checking the acoustic signal for the at least one sound event in order to enable detection of the property or change in state of the dispensing device, wherein said at least one sound generator comprises at least two different sound generators which are designed so that, in different phases of the dispensing process which follow one another in time, a first sound event and a second different sound event are generated.

2. System according to claim 1, wherein the at least one sound generator is designed so that the sound event or the sound events in the dispensing process is generated necessarily and in a reproducible manner.

3. System according to claim 1, wherein the at least one sound generator is a structure that is not required for the dispensing process and/or is specifically designed for the generation of the sound event.

4. System according to claim 1, wherein a protecting element of the dispensing device has or forms the sound generator, wherein the protecting element keeps the substance from being dispensed in an initial state, and wherein generation of the sound event can be transferred into an enabling state for enabling the dispensing of the substance.

5. System according to claim 1, wherein the at least one sound generator is configured for generating a sequence of more than two sound events in the acoustic signal, the sound events being separated from one another and following one another in time in the course of the dispensing process.

6. System according to claim 1, wherein the detection device is designed for detecting the property or change in state of the dispensing device by checking the acoustic signal for the at least one sound event.

7. System according to claim 6, wherein the detection device is designed to compare the acoustic signal to at least one sound event pattern and in this way to detect the at least one sound event in the acoustic signal, wherein sound event patterns are previously known information that corresponds to the sound events, which is similar to the sound events, or is derived therefrom.

8. System according to claim 7, wherein the detection device has a correlation module for generating a correlation of the acoustic signal with the one or more sound event patterns.

9. System according to claim 6, wherein the detection device is designed to determine the property or change in state of the dispensing device when at least one sound event is detected in the acoustic signal based on the detected sound event.

10. System according to claim 1, wherein the detection device has or forms an analysis device for examining multiple sound events, detected in the check, for a predetermined sequence or order.

11. System for monitoring an actual or simulated preparation, performing, and/or post-processing of a dispensing- referred to below as dispensing process—of an administrable, substance, having:
a dispensing device for dispensing the substance, wherein the dispensing device has at least one sound generator, which is designed to generate in the dispensing process at least one sound event in an acoustic signal, the sound event being specific to a property or change in state of the dispensing device, and
a detection device for checking the acoustic signal for the at least one sound event in order to enable detection of the property or change in state of the dispensing device,
wherein the system has multiple dispensing devices, which are distinguished relative to the substance and the sound generator and are otherwise designed identically or similarly, so that identical sound events or acoustic signals can be generated by the identical or similar dispensing devices with the same properties relative to the substance, and different sound events or acoustic signals can be generated by the identical or similar dispensing devices with different properties relative to the substance.

12. Method for detection of a property or change in state of a dispensing device, wherein by means of a mobile terminal device, a Smartphone, a tablet computer, a wearable device, a smartwatch or a fitness arm band, an acoustic signal is checked for at least one sound event that is specific to a property or change in state of the dispensing device, which sound event is generated with a sound generator of the dispensing system in the case of an actual or simulated preparation, performing of a dispensing, or post-processing of a process of dispensing an administrable substance, wherein the sound generator is designed to generate, upon an actual or simulated preparation of dispensing of the substance, at least one reproducible sound event in an acoustic signal, the sound event being specific to a property and/or change in state of the dispensing device.

13. Protecting element for a dispensing device for dispensing an administrable substance, wherein the protecting element has or forms a sound generator which is designed to generate, upon an actual or simulated preparation of dispensing of the substance, at least one reproducible sound event in an acoustic signal, the sound event being specific to a property and/or change in state of the dispensing device, wherein the protecting element has a first and a second part that are movable relative to each other between an initial position and an activation position.

14. Protecting element according to claim 13, wherein the protecting element is at least one of cap-shaped or a cover.

15. Protecting element according to claim 13, wherein the protecting element is configured to keep the substance from being dispensed in an initial state of the dispensing device, and wherein generation of the sound event can be transferred into an enabling state for enabling the dispensing of the substance.

16. Protecting element according to claim 13, wherein the protecting element is configured to generate the sound event upon removing the protecting element from a main body of the dispensing device, and wherein the generated sound event is independent of one or more of the speed, force or other external parameters used for removing the protecting element from the main body.

17. Protecting element according to claim 13, wherein the protecting element has an activation position, wherein the protecting element is configured to one or more of automatically, immediately or necessarily generate the sound event after reaching the activation position, wherein the generated sound event is independent of the manner in which the protecting element is manipulated.

18. Protecting element according to claim 13, wherein the protecting element has a drive element which is configured to be activated by manipulating the protecting element such that one or more of the activation position is reached or to at least one of automatically, immediately or necessarily cause generation of the sound event after the protecting element has reached the activation position.

19. Protecting element according to claim 18, wherein the first part is a cap and the second part is a sleeve arranged within the cap, wherein the protecting element has a latching mechanism or stop for preventing the sleeve from being removed from the cap.

20. Protecting element according to claim 18, wherein the sound generator is configured to generate the sound event after movement of the protecting element from the initial position into the activation position or upon return of the protecting element from the activation position to the initial position.

21. Protecting element according to claim 18, wherein the protecting element has a damping device for controlling, damping and/or reducing the speed and/or acceleration of the movement of the protecting element from the activation position to the initial position.

22. Protecting element according to claim 18, wherein the protecting element has a guide which is configured so that upon movement of the protecting element from the initial position into the activation position, sound generating elements of the sound generator do not interact, and so that upon movement of the protecting element from the activation position to the initial position, the sound generating elements interact and generate the sound event, in particular by mechanical interaction.

23. Protecting element according to claim 13, wherein the sound generator has one or more sound generating elements which are attachable to the protecting element, detachable from the protecting element and/or exchangeable.

24. Protecting element according to claim 13, wherein the sound generator has or is formed by an electroacoustic transducer, wherein the protecting element has a switch and electronics, wherein the switch is configured to be actuated upon removing the protecting element from the main body, and wherein the electronics are configured to control the electroacoustic transducer such that the sound event is generated upon actuation of the switch.

25. Protecting element for a dispensing device for dispensing an administrable substance, wherein the protecting element has or forms a sound generator which is designed to generate, upon an actual or simulated preparation of dispensing of the substance, at least one reproducible sound event in an acoustic signal, the sound event being specific to a property and/or change in state of the dispensing device, wherein the sound generator has or is formed by an electroacoustic transducer, wherein the protecting element has a switch and electronics, wherein the switch is configured to be actuated upon removing the protecting element from the main body, and wherein the electronics are configured to control the electroacoustic transducer such that the sound event is generated upon actuation of the switch, and wherein the sound generator or electroacoustic transducer is configured to generate a sound event having a frequency in the ultrasonic range, in particular a frequency of approximately or at least 20 KHz.

26. Dispensing device for dispensing an administrable substance, the dispensing device having a main body and a protecting element, wherein the dispensing device has at least one sound generator, which is designed to generate, upon an actual or simulated preparation of a dispensing of the substance, at least one reproducible sound event in an acoustic signal, the sound event being specific to a property and/or change in state of the dispensing device, wherein the protecting element has or forms a sound generator which is designed to generate, upon an actual or simulated preparation of dispensing of the substance, at least one reproducible sound event in an acoustic signal, the sound event being specific to a property and/or change in state of the dispensing device, wherein the protecting element has a first and a second part that are movable relative to each other between an initial position and an activation position.

27. Dispensing device according to claim 26, wherein the dispensing device is configured to move the protecting element into the activation position upon a process of removing the protecting element and/or the first part from the main body.

28. Dispensing device according to claim 26, wherein the dispensing device is configured to hold the second part in a fixed position relative to the main body upon a process of removing the protecting element and/or the first part from the main body, while the protecting element is moved from the initial position to the activation position by moving the first part relative to the second part and/or the main body.

29. Dispensing device according to claim 26, wherein the dispensing device is configured to release the second part when the protecting element has reached the activation position or activation position and the protecting element and/or first part is further moved away from the main body.

30. System for monitoring an actual or simulated preparation, performing, and/or post-processing of dispensing an administrable substance, comprising:
  a dispensing device for dispensing the substance, wherein the dispensing device has at least one sound generator, which is designed to generate in the dispensing process at least one sound event in an acoustic signal, the sound event being specific to a property or change in state of the dispensing device, and
  a detection device for checking the acoustic signal for the at least one sound event in order to make possible a detection of the property or change in state of the dispensing device, wherein the system has a dispensing device having a main body and a protecting element, wherein the dispensing device has at least one sound generator, which is designed to generate, upon an actual or simulated preparation of a dispensing of the substance, at least one reproducible sound event in an acoustic signal, the sound event being specific to a property and/or change in state of the dispensing device, wherein the protecting element has or forms a sound generator which is designed to generate, upon an actual or simulated preparation of dispensing of the substance, at least one reproducible sound event in an acoustic signal, the sound event being specific to a property and/or change in state of the dispensing device,
  wherein the protecting element has a first and a second part that are movable relative to each other between an initial position and an activation position.

31. Method according to claim 12, wherein the dispensing device has a main body and a protecting element, and wherein the protecting element has a first and a second part that are movable relative to each other between an initial position and an activation position.

32. Method according to claim 12, wherein the sound generator comprises at least two different sound generators which are designed so that, in different phases of the dispensing process which follow one another in time, a first sound event and a second different sound event are generated.

* * * * *